United States Patent [19]
Gotschlich

[11] Patent Number: 5,945,322
[45] Date of Patent: *Aug. 31, 1999

[54] GLYCOSYLTRANSFERASES FOR BIOSYNTHESIS OF OLIGOSACCHARIDES, AND GENES ENCODING THEM

[75] Inventor: Emil C. Gotschlich, New York, N.Y.

[73] Assignee: The Rockefeller University, New York, N.Y.

[ * ] Notice: This patent is subject to a terminal disclaimer.

[21] Appl. No.: 08/878,360

[22] Filed: Jun. 18, 1997

Related U.S. Application Data

[60] Continuation of application No. 08/683,426, Jul. 18, 1996, Pat. No. 5,705,367, which is a division of application No. 08/312,387, Sep. 24, 1994, Pat. No. 5,545,553.

[51] Int. Cl.$^6$ .............................. C12N 9/10; C12N 1/20; C12N 15/00; C07H 21/04
[52] U.S. Cl. ................ 435/193; 435/252.3; 435/254.11; 435/320.1; 435/325; 536/23.2; 536/24.3
[58] Field of Search ........................... 435/6, 172.3, 193, 435/252.3, 254.11, 325, 320.1; 536/23.2, 24.3

[56] References Cited

U.S. PATENT DOCUMENTS 5,180,674  1/1993  Roth ........................................ 435/288

FOREIGN PATENT DOCUMENTS

WO 93/13198  7/1993  WIPO .

OTHER PUBLICATIONS

Sandlin & Stein, 1994, *J. Bacteriol.* 176:2930–2937.
Zhou et al., 1994, *J. Biol. Chem.* 269:11162–11169.
Gibson et al., 1993, *J. Bacteriol.* 175:2702–2712.
Jennings et al., 1993, *Molec. Microbiol.* 19:361–369.
High et al., 1993, *Molec. Microbiol.* 9:1275–1282.
Robertson et al., 1993, *Molec. Microbiol.* 8:891–901.
van Putten et al., 1993, *EMBO J.* 12:4043–4051.
Verheul et al., 1993, *Microbiol, Rev.* 57:34–49.
Yamasaki et al., 1993, *J. Bacteriol.* 175:4565–4568.
Kerwood et al., 1992, *Biochem.* 31:12760–12768.
Knight et al., 1992, *Molec. Microbiol.* 6:1565–1573.
Mandrell, 1992, *Infect. Immunol.* 60:3017–3020.
Pradel et al., 1992, *J. Bacteriol.* 174:4736–4745.
Cope et al., 1991, *Molec. Microbiol.* 5:1113–1124.
John et al., 1981, *J. Biol. Chem.* 266:19303–19311.
Jonsson et al., 1991, *EMBO J.* 10:477–488.
Mandrell et al., 1991, *J. Bacteriol.* 173:2823–2832.
Schneider et al., 1991, *J. Exp. Med.* 174:1601–1605.
Tsai & Civin, 1991, *Infect. Immun.* 59:3604–3609.
Mandrell et al., 1990, *J. Exp. Med.* 171:1649–1664.
Parsons et al., 1989, *Microb. Pathog.* 7:63–72.
Dudas & Apicella, 1988, *Infect. Immun.* 56:499–504.
Mandrell et al., 1988, *J. Exp. Med.* 168:107–126.
Schneider et al., 1988, *Infect. Immun.* 56:942–946.
Apicella et al., 1987, *Infect. Immun.* 55:1755–1761.
Webster et al., 1983, *J. Biol. Chem.* 258:10637–10641.
Gotschlich, 1994, *J. Exp. Med,* 180:2181–2190.
Stephens et al., 1994, *Infect. & Immun.* 2:2947–2952.
Zhou et al., 1994, *Molec. Microbiol.* 14:609–618.

*Primary Examiner*—Lisa Hobbs
*Attorney, Agent, or Firm*—Pennie & Edmonds LLP

[57] ABSTRACT

The present invention is directed to nucleic acids encoding glycosyltransferases, the proteins encoded thereby, and to methods for synthesizing oligosaccharides using the glycosyltransferases of the invention. In particular, the present application is directed to identification a glycosyltransferase locus of *Neisseria gonorrhoeae* containing five open reading frames for five different glycosyltransferases. The functionally active glycosyltransferases of the invention are characterized by catalyzing reactions such as adding Gal β1→4 to GlcNAc or Glc; adding GalNAc or GlcNAc β1→3 to Gal; and adding Gal α1→4 to Gal. The glycosyltransferases of the invention are particularly suited to the synthesis of the oligosaccharides Galβ1→4GlcNAcβ1→3Galβ1→4Glc (a mimic of lacto-N-neotetraose), GalNAcβ1→3Galβ1→4GlcNAcβ1→3Galβ1→4Glcβ1→4 (a mimic ganglioside), and Galα1→4Galβ1→4Glcβ1→4Hep→R (a mimic of the saccharide portion of globo-glycolipids).

20 Claims, 18 Drawing Sheets

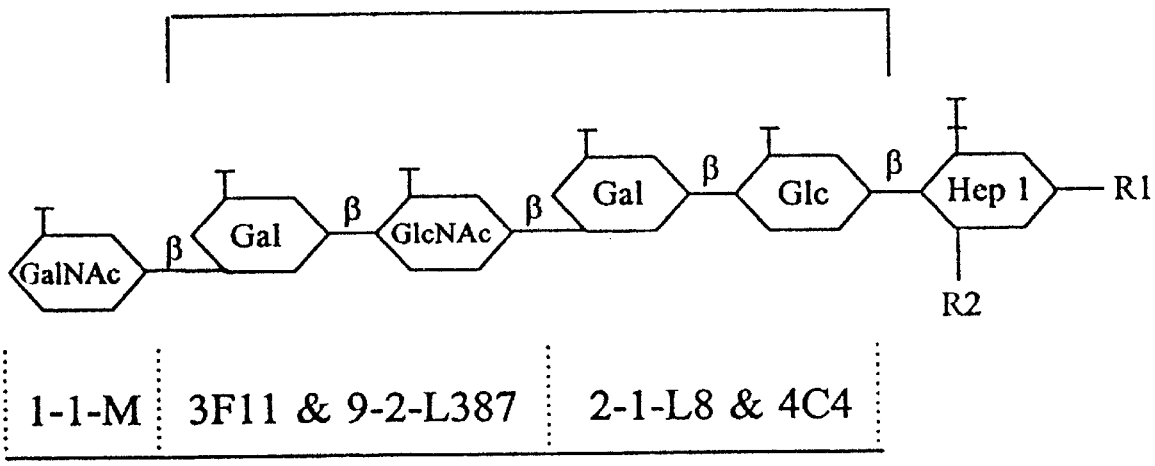
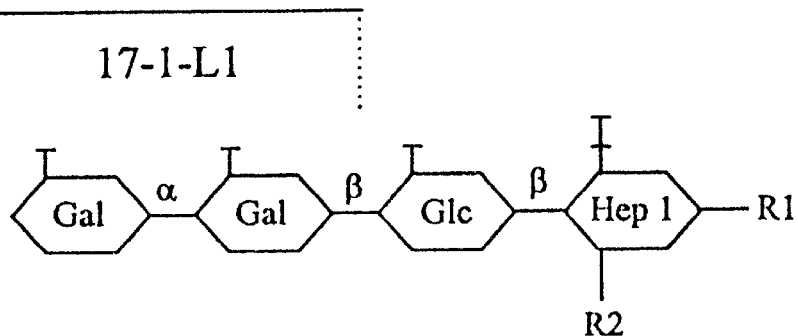
FIG. 1

FIG.2B-1

```
SOURCE      Neisseria gonorrhoeae.
ORGANISM    Neisseria gonorrhoeae
    source          1..5859
    CDS             <1..381
                    /gene="glyS"
                    /codon_start=1
                    /transl_table=11
                    /product="glycyl tRNA synthetase beta chain"
                    /translation="LQAVAVFKQLPEAAALAAANKRVQNLLKKADAALGEVNESLLQQ
                    DEEKALYAAAQGLQPKIAAAVAEGNFRTALSELASVKPQVDAFFDGVMVMAEDAAVKQ
                    NRLNLLNRLAEQMNAVADIALLGE"
    CDS             445..1491
                    /gene="lgtA"
                    /codon_start=1
                    /function="adds GlcNAc to lacto-N-neotetraose chain of
                    gonococcal LOS"
                    /evidence=experimental
                    /transl_except=(pos:445..447,aa:Met)
                    /transl_table=11
                    /product="glycosyl transferase"
                    /translation="MQPLVSVLICAYNVEKYFAQSLAAVVNQTWRNLDILIVDDGSTD
                    GTLAIAKDFQKRDSRIKILAQAQNSGLIPSLNIGLDELAKSGGGGEYIARTDADDIA
                    SPGWIEKIVGEMEKDRSIIAMGAWLEVLSEEKDGNRLARHHHGKIWKKPTRHEDIAA
                    FFPFGNPIHNNTMIMRRSVIDGGLRYDTERDWAEDYQFWYDVSKLGRLAYYPEALVKY
                    RLHANQVSSKHSVRQHEIAQGIQKTARNDFLQSMGFKTRFDSLEYRQTKAAAYELPEK
                    DLPEEDFERARRFLYQCFKRTDTPPSGAWLDFAADGRMRRLFTLRQYFGILYRLIKNR
                    RQARSDSAGKEQEI"
```

FIG.2B-2

```
CDS    1491..2330
       /gene="lgtB"
       /codon_start=1
       /function="adds second galactose to the lacto-N-tetraose
       chain in LOS"
       /evidence=experimental
       /product="glycosyl transferase"
```

/translation="MQNHVISLASAAERRAHIAATFGSRGIPFQFFDALMPSERLERA
MAELVPGLSAHPYLSGVEKACFMSHAVLWEQALDEGVPYIAVFEDDVLLGEGAEQFLA
EDTWLQERFDPDSAFVVRLETMFMHVLTSPSGVADYGGRAFPLLESEHCGTAGYIISR
KAMRFFLDRFAVLPPERLHPVDLMMFGNPDDREGMPVCQLNPALCAQELHYAKFHDQN
SALGSLIEHDRRLNRKQQWRDSPANTFKHRLIRALTKIGREREKRRQRREQLIGKIIV
PFQ"

```
CDS    2342..3262
       /gene="lgtC"
       /codon_start=1
       /function="adds galactose alpha(1-4) to Gal-Glc in
       gonococcal LOS"
       /evidence=experimental
       /transl_table=11
       /product="glycosyl transferase"
```

/translation="MDIVFAADDNYAAYLCVAAKSVEAAHPDTEIRFHVLDAGISEEN
RAAVAANLRGGGNIRFIDVNPEDFAGFPLNIRHISITTYARLKLGEYIADCDKVLYLD
TDVLVRDGLKPLWDTDLGGNWVGACIDLFVERQEGYKQKIGMADGEYYFNAGVLLINL
KKWRRHDIFKMSCEWVEQYKDVMQYQDQDILNGLFKGGVCYANSRFNFMPTNYAFMAN
GFASRHTDPLYLDRTNTAMPVAVSHYCGSAKPWHRDCTVWGAERFTELAGSLTTVPEE
WRGKLAVPPTKCMLQRWRKKLSARFLRKIY"

FIG.2B-3

```
CDS        3322..4335
           /gene="lgtD"
           /codon_start=1
           /function="adds terminal GalNAc to lacto-N-neotetraose
           chain of LOS"
           /evidence=experimental
           /transl_except=(pos:3322..3324,aa:Met)
           /transl_table=11
           /product="glycosyl transferase"
```

/translation="MQPLVSVLICAYNAEKYFAQSLAAVVGQTWRNLDILIVDDGSTD
GTPAIARHFQEQDGRIRIISNPRNLGFIASLNIGLDELAKSGGGEYIARTDADDIASP
GWIEKIVGEMEKDRSIIAMGAWLEVLSEENNKSVLAAIARNGAIWDKPTRHEDIVAVF
PFGNPIHNNTMIMRRSVIDGGLRFDPAYIHAEDYKFWYEAGKLGRLAYYPEALVKYRF
HQDQTSSKYNLQQRRTAWKIKEEIRAGYWKAAGIAVGADCLNYGLLKSTAYALYEKAL
SGQDIGCLRLFLYEYFLSLEKYSLTDLLDFLTDRVMRKLFAAPQYRKILKKMLRPWKY
RSY"

```
CDS        4354..5196
           /gene="lgtE"
           /codon_start=1
           /function="adds first galactose to lacto-N-neotetraose
           chain of LOS"
           /evidence=experimental
           /transl_table=11
           /product="glycosyl transferase"
```

/translation="MQNHVISLASAAERRAHIADTFGSRGIPFQFFDALMPSERLEQA
MAELVPGLSAHPYLSGVEKACFMSHAVLWEQALDEGLPYIAVFEDDVLLGEGAEQFLA
EDTWLEERFDKDSAFIVRLETMFAKVIVRPDKVLNYENRSFPLLESEHCGTAGYIISR
EAMRFFLDRFAVLPPERIKAVDLMMFTYFFDKEGMPVYQVSPALCTQELHYAKFLSQN
SMLGSDLEKDREQGRRHRRSLKVMFDLKRALGKFGREKKKRMERQRAELEKVYGRRV
ILFK"

FIG.2B-4

```
BASE COUNT     1412 a    1462 c    1661 g    1324 t
ORIGIN
    1 ctgcaggccg tcgccgtatt caaacaactg cccgaagccg ccgcgctcgc cgccgccaac
   61 aaacgcgtgc aaaacctgct gaaaaaagcc gatgccgcgt tgggcgaagt caatgaaagc
  121 ctgctgcaac aggacgaaga aaaagccctg tacgctgccg cgcaaggttt gcagccgaaa
  181 attgccgccg ccgtcgccga aggcaatttc cgaaccgcct tgtccgaact ggcttccgtc
  241 aagccgcagg ttgatgcctt cttcgacggc gtgatggtga tgcggaaga tgccgccgta
  301 aaacaaaacc gcctgaacct gctgaaccgc ttggcagagc agatgaacgc ggtggccgac
  361 atcgcgcttt tgggcgagta accgttgtac agtccaaatg ccgtctgaag cctcaggcg
  421 gcatcaaatt atcgggagag taaattgcag ccttagtca gcgtattgat ttgcgcctac
  481 aacgtagaaa aatattttgc ccaatcatta gccgccgtcg tgaatcagac ttggcgcaac
  541 ttggatattt tgattgtcga tgacggctcg acagacggca cacttgccat tgccaaggat
  601 tttcaaaagc gggacagccg tatcaaaatc cttgcacaag ctcaaaattc cggcctgatt
  661 ccctctttaa acatcgggct ggacgaattg gcaaagtcgg gggggggg gggggaatat
  721 attgcgcgca ccgatgccga cgatattgcc tccccggct gattgagaa aatcgtggc
  781 gagatgaaa aagaccgcag catcattgcg atgggcgcgt gctggaagt tttgtcggaa
  841 gaaaaggacg gcaaccggct ggcgcggcac cacaaacacg gcaaaatttg gaaaaagccg
  901 acccggcacg aagacatcgc cgccttttc cctttcggca acccataca caacaacacg
  961 atgattatgc ggcgcagcgt cattgacggc ggtttgcgtt acgacaccga gcgggattgg
 1021 gcggaagatt accaattttg gtacgatgtc agcaaattgg gcaggctggc ttattatccc
 1081 gaagccttgg tcaaataccg cctcacgcc aatcaggttt catccaaaca cagcgtccgc
 1141 caacacgaaa tcgcgcaagg catccaaaaa accgccagaa acgatttttt gcagtctatg
 1201 ggttttaaaa cccgttcga cagcctagaa caaaagcagc ggcgtatgaa
 1261 ctgccggaga aggatttgcc ggaagaagat tttgaacgcg cccgccgtt tttgtaccaa
 1321 tgcttcaaac ggacggacac gccgccctcc ggcgcgtggc tggatttcgc ggcagacggc
 1381 aggatgaggc ggctgtttac cttgaggcaa tacttcggca tttgtaccg gctgattaaa
 1441 aaccgccggc aggcgcggtc ggattcggca gggaaagaac aggagattta atgcaaaacc
 1501 acgttatcag cttggcttcc gccgcagaac gcagggcgca cattgccgca accttcggca
 1561 gtcgcggcat cccgttccag ttttcgacg cactgatgcc gtctgaaagg ctgaacgggg
```

FIG.2B-5

```
1621 caatgcgga actcgtcccc ggcttgtcgg cgcacccta tttgagcgga gtggaaaaag
1681 cctgctttat gagccacgcc gtattgtggg aacaggcatt ggacgaaggc gtaccgtata
1741 tcgccgtatt tgaagatgat gtcttactcg gcgaaggcgc ggagcagttc cttgccgaag
1801 atacttggct gcaagaacgc tttgacccg attccgcctt tgtcgtccgc ttgaaacga
1861 tgtttatgca cgtcctgacc tcgccctccg gcgtggcgga ctacggcggg cgcgcctttc
1921 cgcttttgga aagcgaacac tgcgggacgg cgggctatat tatttcccga aaggcgatgc
1981 gttttttctt ggacagtttt gccgtttttgc cgcccgaacg cctgcaccct gtcgatttga
2041 tgatgttcgg caaccctgac gacaggaag gaatgccggt ttgccagctc aatcccgcct
2101 tgtgcgccca agagctgcat tatgccaagt ttcacgacca aaacagcgca ttggcagcc
2161 tgatcgaaca tgaccgccgc ctgaaccgca aacagcaatg gcgcgattcc cccgccaaca
2221 cattcaaaca ccgcctgatc cgcgcccttga ccaaaatcgg caggaaagg gaaaaacgcc
2281 ggcaaaggcg cgaacagtta atcggcaaga ttattgtgcc tttccaataa aaggagaaaa
2341 gatgacatc gtatttgcgg cagacgacaa ctatgccgcc taccttttgcg ttgcggcaat
2401 aagcgtgaa gcggcccatc ccgatacgga aatcaggttc cacgtcctcg atgccggcat
2461 cagtgaggaa aacccgcggg cggttgccgc caatttgccgg ggggggta acattttccat
2521 tatagacgta gacgtattgg atttcgccgg cttccccta aacattgcc aagtcctggg
2581 tacgacttat gcccgcctga aattgggcga atacattgcc cctgaagccc ccgatttggg
2641 tctggatacg gacgtattgg tcaggacgg gcatcgattt gtttgtcgaa ttatgggata gatacaaaca
2701 cggtaactgg gtcggcgcgt atggcggacg gagaatatata tttcaatgcc ggcgtattgc tgatcaacct
2761 aaaaatcggt atggcggacg gagaatatata atatttcaa aatgtcctgc gaatgggtgg aacaatacaa
2821 gaaaaagtgg cggcggcacg caatatcagg atcaggacat tttgaacggg ctgtttaaaag gcgggtgtg
2881 ggacgtgatg caatatcagg agtgtatgct acttatgcc gaccaattat gcctttatgg cgaacgggtt
2941 ttatgcgaac agccgtttca acttatgcc gaccaattat gcctttatgg cgaacgggtt
3001 tgcgtcccgc cataccgacc cgctttaccct cgaccgtacc aatacggcga tgcccgtcgc
3061 cgtcagccat tattgcggct cggcaaagcc gtggcacagg gactgcaccg tttggggtgc
3121 ggaacgtttc acagagttgg ccggcagcct gacgaccgtt cccgaagaat ggcgcggcaa
3181 acttgccgtc ccgccgacaa agtgtatgct tcaaagatgg cgcaaaaagc tgtctgccag
3241 attcttacgc aagatttatt gacggggcag gccgtctgaa gccttcagac ggcatcggac
3301 gtatcggaaa ggagaaacgg attgcagcct ttagtcagcg tattgattttg cgcctacaac
3361 gcagaaaaat atttgccca atcattggcc gccgtagtgg ggcagacttg gcgcaacttg
```

FIG.2B-6

```
3421 gatatttga ttgtcgatga cggctcgacg gacggcacgc cgccattgc ccggcattc
3481 caagaacagg acggcaggat caggataatt tccaatcccc gcaatttggg ctttatcgcc
3541 tctttaaaca tcgggctgga cgaattggca aagtcggggg gggggaata tattgcgcgc
3601 accgatgccg acgatattgc ctcccccggc tggattgaga aaatcgtggg cgagatggaa
3661 aaagaccgca gcatcattgc gatgggcgcg tggttggaag tgggtcgga agaaaacaat
3721 aaaagcgtgc ttgccgccat tgcccgaaac ggcgcaattt gggacaaacc gacccggcat
3781 gaagacattg tcgccgtttt cccttccggc aaccccatac acaacaacac gatgattatg
3841 aggcgcagcg tcattgacgg cgtttgcgg ttcgatccag cctatatcca cgccgaagac
3901 tataagtttt ggtacgaagc cggcaaactg ggcaggctgg cttattatcc cgaagccttg
3961 gtcaaatacc gcttccatca agaccagact tcttccaaat acaacctgca acagcgcagg
4021 acggcgtgga aaatcaaaga agaaatcagg gcgggtatt ggaaggcggc aggcatagcc
4081 gtcggggcgg actgcctgaa ttacggcgtt ttgaaatcaa cggcatatgc gttgtacgaa
4141 aaagccttgt ccggacagga tatcggatgc ctccgcctgt tcctgtacga atatttcttg
4201 tcgttgaaa agtattcttt gaccgatttg ctgatttct tgacagaccg cgtgatgagg
4261 aagctgtttg ccgcaccgca atataggaaa atcctgaaaa aaatgttacg cccttggaaa
4321 taccgcagct attgaaaccg aacaggataa atcatgcaaa accacgttat cagcttggct
4381 tccgcccgcag agcgcaggge gcacattgcc gatacccttcg gcagtcgcgg catcccgttc
4441 cagttttcg acgcactgat gccgtctgaa aggctggaac aggcgatggc ggaactcgtc
4501 cccggcttgt cggcgcaccc ctatttgagc ggagtggaaa aagcctgctt tatgagccac
4561 gccgtattgt gggaacaggc gttggatgaa ggtctgccgt atatcgccgt atttgaggac
4621 gacgttttac tcggcgaagg cgcggagcag ttccttgccg aagatacttg gttggaagag
4681 cgttttgaca aggattccgc ctttatcgtc cgtttgggaaa cgatgtttgc gaaagttatt
4741 gtcagaccgg ataaagtcct gaattatgaa aaccggtcat ttccttttgct ggagagcgaa
4801 cattgtggga cggctggcta tatcatttcg cgtgaggcga tgcggtttttt cttggacagg
4861 tttgccgttt tgccgccaga gcggattaaa gcggtagatt tgatgatgtt tacttatttc
4921 tttgataagg aggggatgcc tgtttatcag gttagtcccg gttgtgtac ccttatgtac ccaagaattg
4981 cattatgcca agttctcag tcaaacagt atgttgggta gcgatttgga aaaagatagg
5041 gaacaaggaa gaagacaccg ccgttcgttg aagtgatgt ttgacttgaa gcgtgctttg
5101 ggtaaattcg gtagggaaaa gaagaaaaga atggagcgtc aaaggcaggc ggagcttgag
5161 aaagtttacg gcaggcgggt catattgttc aaatagtttc tgtaaaatat aggggattaa
```

FIG.2B-7

```
5221  aatcagaaat ggacacactg tcattcccgc gcaggcggga atctaggtct ttaaacttcg
5281  gtttttccg  ataaattctt gccgcattaa aattccagat tcccgctttc gcggggatga
5341  cggcggggg  attgttgctt tttcggataa aatcccgtgt tttttcatct gctaggtaaa
5401  atcgccccaa agcgtctgca tcgcggcgat ggcggcgagt gggcggttt  ctgtgcgtaa
5461  aatccgtttt ccgagtgtaa ccgcctgaaa gccggcttca aatgcctgtt gttcttcctg
5521  ttctgtccag ccgccttcgg gcccgaccat aaagacgatt gcgccggacg ggtggcggat
5581  gtcgccgagt ttgcaggcgc ggttgatgct cataatcagc ttggtgtttt cagacggcat
5641  tttgtcgagt gcttcacggt agccgatgat gggcagtacg ggggaacgg  tgttcctgcc
5701  gctttgttcg cacgcggaga tgacgatttc ctgccagcgt gcgaggcgtt tggcggcgcg
5761  ttctccgtcg aggcggacga tgcagcgttc gctgatgacg ggctgtatgg cggttacgcc
5821  gagttcgacg cttttttgca gggtgaaatc catgcgatc
```

```
lgtA   1  LQPLVSVLICAYNVEKYFAQSLAAVVNQTWRNLDILIVDDGSTDGTLAIA   50
          ::::::::::::::::::::::::::::::::::::::::::::::::::
lgtD   1  LQPLVSVLICAYNAEKYFAQSLAAVVGQTWRNLDILIVDDGSTDGTPAIA   50 lgtA  51  KDFQKRDSRIKILAQAQNSGLIPSLNIGLDELAKSGGGGGGEYIARTDADD  100
          :::::::::::::::::::::::::::::::::::::::::::::::::
lgtD  51  RHFQEQDGRIRIISNPRNLGFIASLNIGLDELAKS..GGGEYIARTDADD   98 lgtA 101  IASPGWIEKIVGEMEKDRSIIAMGAWLEVLSEEKDGNRLARHHKHGKIWK  150
          ::::::::::::::::::::::::::::::::::::::::::::::::::
lgtD  99  IASPGWIEKIVGEMEKDRSIIAMGAWLEVLSEENNKSVLAAIARNGAIWD  148 lgtA 151  KPTRHEDIAAFFPFGNPIHNNTMIMRRSVIDGGLRYDTERDWAEDYQFWY  200
          ::::::::::::::::::::::::::::::::::::::::::::::::::
lgtD 149  KPTRHEDIVAVFPFGNPIHNNTMIMRRSVIDGGLRFDPAYIHAEDYKFWY  198
```

FIG. 3A

```
lgtA  201  DVSKLGRLAYYPEALVKYRLHANQVSSKHSVRQHEIAQGIQKTARNDFLQ  250
              :||:||||||||||||||||:|  :  :   :  : |  |:  ::
lgtD  199  EAGKLGRLAYYPEALVKYRFHQDQTSSKYNLQQRRTAWKIKEEIRAGYWK  248 lgtA  251  SMGFKTRFDSLEYRQTKAAAYELPEKDLPEEDFERARRFLYQCFKRTDTP  300
              :    :  ::    |  :  :|| |:|  |   |:|| |:
lgtD  249  AAGIAVGADCLNYGLLKSTAYALYEKALSGQDIGCLRLFLYEYFLSLEKY  298 lgtA  301  PSGAWLDFAADGRMRRLFTLRQYFGILYRLIKNRR  335
             :  ::|| :  |:|:|| ||:|:|:| |:|
lgtD  299  SLTDLLDFLTDRVMRKLFAAPQYRKILKKMLRPWK  333
```

FIG.3B

```
lgtB    1  MQNHVISLASAAERRAHIADTFGSRGIPFQFFDALMPSERLEQAMAELVP   50
           ||||||||||||||||||||||||||||||||||||||||||||||||||
lgtE    1  MQNHVISLASAAERRAHIADTFGSRGIPFQFFDALMPSERLEQAMAELVP   50 lgtB   51  GLSAHLYLSGVEKACFMSHAVLWEQALDEGLPYIAVFEDDVLLGEGAEQF  100
           |||||:|||||||||||||||||||||||||||||||||||||||||||
lgtE   51  GLSAHPYLSGVEKACFMSHAVLWEQALDEGLPYIAVFEDDVLLGEGAEQF  100 lgtB  101  LAEDTWLQERFDPDSAFVVRLETMFMHVLTSPSGVADYGGRAFPLLESEH  150
           |||||||:||||:||||:||||||| :  : : . .:||.|||||||||
lgtE  101  LAEDTWLEERFDKDSAFIVRLETMFAKVIVRPDKVLNYENRSFPLLESEH  150 lgtB  151  CGTAGYIISRKAMRFFLDRFAVLPPERLHPVDLMMFGNPDDREGMPVCQL  200
           |||||||||| ||||||||||||||||: . :.||: :|:|||||| ||
lgtE  151  CGTAGYIISREAMRFFLDRFAVLPPERIKAVDLMMFTYFFDKEGMPVYQV  200
```

FIG. 4A

```
lgtB 201 NPALCAQELHYAKFHDQNSALGSLIEHDRRLNRKQQRRDSPANTFKHRLI 250
             :||||| ||||||:||:: || : ||  :   :|| : ::  :|
lgtE 201 SPALCTQELHYAKFLSQNSMLGSDLEKD.....REQGRRHRRSLKVMFDLK 246 lgtB 251 RALTKIGREREKRRKRR......EQTIGKIIVPFQ 279
         ||| : |||:|:|::||      :  :|:| |:|
lgtE 247 RALGKFGREKKKRMERQRQAELEKVYGRRVILFK 280
```

FIG.4B

```
rfaI   29  LDIAYGTDKNFLFGCCGISIASILKYNEGSRLCFHIFTDYFGDDDRKYFDA   78
            :| :::|: :|:     |   :    : ::::
lgtC    1  MDIVFAADDNYAAYLCVAAKSVEAAHPDTEIRFHVLDAGISEENRAAVAA   50 rfaI   79  LALQYKTRIKIYLINGDRLRSLP.STKNWTHAIYFRFVIADYFINKAPKV  127
            :   |:::|:||  :::|: |: ::    ::::|:| :
lgtC   51  .NLRGGNIRFIDVNPEDFAGFPLNIRHISITTYARLKLGEY.IADCDKV   98 rfaI  128  LYLDADIICQGTIEPLINFSFPDDKVAMVV....TEGQADWWEKRAHSLGV  174
            |||| |:  :  ::: ::|::    :: ::                 :|:
lgtC   99  LYLDTDVLVRDGLKPLWDTDLGGNWVGACIDLFVERQEGYKQK....IGM  144 rfaI  175  AGIAKGYFNSGFLLINTAQWAAQQVSARAIAMLNEPEIIKKITHPDQDVL  224
            |: :||||||| |::: | : :::|::  ::|::|: :::|::
lgtC  145  AD.GEYYFNAGVLLINLKKWRRHDIFKMSCEWVEQYKDVMQ..YQDQDIL  191
```

FIG. 5A

```
rfaI 225 NMLLADKLIFADIKYNTQFSLNYQLKESFINPVTNDTIFI............ 264
lgtC 192 NGLFKGGVCYANSRFNF.MPTNYAFMANGFASRHTDPLYLDRTNTAMPVA 240 rfaI 265 ..HYIGPTKPWHDWAWDYPVSQAFMEAKNASPWKNTALLKPNNSNQLRYS 312
lgtC 241 VSHYCGSAKPWH...RDCTVWGAERFTELAGSL..TTVPEEWRGKLAVPP 285 rfaI 313 AKHMLKKHRYLKGFSNYLFYFI 334
lgtC 286 TKCML..QRWRKKLSARFLRKI 305
```

FIG.5B

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 5859 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Neisseria gonorrheae
        (B) STRAIN: F62

(ix) FEATURE:
        (A) NAME/KEY: CDS
        (B) LOCATION: 1..381
        (D) OTHER INFORMATION: glys (glycyl tRNA syntetase beta chain)

(ix) FEATURE:
        (A) NAME/KEY: CDS
        (B) LOCATION: 445..1491
        (D) OTHER INFORMATION: lgtA (ix) FEATURE:
        (A) NAME/KEY: CDS
        (B) LOCATION: 2342..3262
        (D) OTHER INFORMATION: lgtC (ix) FEATURE:
        (A) NAME/KEY: CDS
        (B) LOCATION: 3322..4335
        (D) OTHER INFORMATION: lgtD (ix) FEATURE:
        (A) NAME/KEY: CDS
        (B) LOCATION: 4354..5196
        (D) OTHER INFORMATION: lgtE (xi) SEQUENCE DESCRIPTION: SEQ ID NO:1:

```
CTG CAG GCC GTC GCC GTA TTC AAA CAA CTG CCC GAA GCC GCC GCG CTC        48
Leu Gln Ala Val Ala Val Phe Lys Gln Leu Pro Glu Ala Ala Ala Leu
 1               5                  10                  15

GCC GCC GCC AAC AAA CGC GTG CAA AAC CTG CTG AAA AAA GCC GAT GCC        96
Ala Ala Ala Asn Lys Arg Val Gln Asn Leu Leu Lys Lys Ala Asp Ala
                20                  25                  30

GCG TTG GGC GAA GTC AAT GAA AGC CTG CTG CAA CAG GAC GAA GAA AAA       144
Ala Leu Gly Glu Val Asn Glu Ser Leu Leu Gln Gln Asp Glu Glu Lys
            35                  40                  45

GCC CTG TAC GCT GCC GCG CAA GGT TTG CAG CCG AAA ATT GCC GCC GCC       192
Ala Leu Tyr Ala Ala Ala Gln Gly Leu Gln Pro Lys Ile Ala Ala Ala
 50                  55                  60

GTC GCC GAA GGC AAT TTC CGA ACC GCC TTG TCC GAA CTG GCT TCC GTC       240
Val Ala Glu Gly Asn Phe Arg Thr Ala Leu Ser Glu Leu Ala Ser Val
65                  70                  75                  80

AAG CCG CAG GTT GAT GCC TTC TTC GAC GGC GTG ATG GTG ATG GCG GAA       288
Lys Pro Gln Val Asp Ala Phe Phe Asp Gly Val Met Val Met Ala Glu
                85                  90                  95

GAT GCC GCC GTA AAA CAA AAC CGC CTG AAC CTG CTG AAC CGC TTG GCA       336
Asp Ala Ala Val Lys Gln Asn Arg Leu Asn Leu Leu Asn Arg Leu Ala
                100                 105                 110

GAG CAG ATG AAC GCG GTG GCC GAC ATC GCG CTT TTG GGC GAG TAACCGTTGT    388
Glu Gln Met Asn Ala Val Ala Asp Ile Ala Leu Leu Gly Glu
            115                 120                 125

ACAGTCCAAA TGCCGTCTGA AGCCTTCAGG CGGCATCAAA TTATCGGGAG AGTAAA         444
```

| | | |
|---|---|---|
| TTG CAG CCT TTA GTC AGC GTA TTG ATT TGC GCC TAC AAC GTA GAA AAA<br>Met Gln Pro Leu Val Ser Val Leu Ile Cys Ala Tyr Asn Val Glu Lys<br>1                        5                       10                      15 | 492 |
| TAT TTT GCC CAA TCA TTA GCC GCC GTC GTG AAT CAG ACT TGG CGC AAC<br>Tyr Phe Ala Gln Ser Leu Ala Ala Val Val Asn Gln Thr Trp Arg Asn<br>                  20                       25                       30 | 540 |
| TTG GAT ATT TTG ATT GTC GAT GAC GGC TCG ACA GAC GGC ACA CTT GCC<br>Leu Asp Ile Leu Ile Val Asp Asp Gly Ser Thr Asp Gly Thr Leu Ala<br>             35                       40                      45 | 588 |
| ATT GCC AAG GAT TTT CAA AAG CGG GAC AGC CGT ATC AAA ATC CTT GCA<br>Ile Ala Lys Asp Phe Gln Lys Arg Asp Ser Arg Ile Lys Ile Leu Ala<br>    50                       55                       60 | 636 |
| CAA GCT CAA AAT TCC GGC CTG ATT CCC TCT TTA AAC ATC GGG CTG GAC<br>Gln Ala Gln Asn Ser Gly Leu Ile Pro Ser Leu Asn Ile Gly Leu Asp<br>65                       70                       75                     80 | 684 |
| GAA TTG GCA AAG TCG GGG GGG GGG GGG GAA TAT ATT GCG CGC ACC<br>Glu Leu Ala Lys Ser Gly Gly Gly Gly Glu Tyr Ile Ala Arg Thr<br>                         85                       90                     95 | 732 |
| GAT GCC GAC GAT ATT GCC TCC CCC GGC TGG ATT GAG AAA ATC GTG GGC<br>Asp Ala Asp Asp Ile Ala Ser Pro Gly Trp Ile Glu Lys Ile Val Gly<br>            100                    105                    110 | 780 |
| GAG ATG GAA AAA GAC CGC AGC ATC ATT GCG ATG GGC GCG TGG CTG GAA<br>Glu Met Glu Lys Asp Arg Ser Ile Ile Ala Met Gly Ala Trp Leu Glu<br>        115                    120                    125 | 828 |
| GTT TTG TCG GAA GAA AAG GAC GGC AAC CGG CTG GCG CGG CAC CAC AAA<br>Val Leu Ser Glu Glu Lys Asp Gly Asn Arg Leu Ala Arg His His Lys<br>    130                     135                    140 | 876 |
| CAC GGC AAA ATT TGG AAA AAG CCG ACC CGG CAC GAA GAC ATC GCC GCC<br>His Gly Lys Ile Trp Lys Lys Pro Thr Arg His Glu Asp Ile Ala Ala<br>145                     150                    155                  160 | 924 |
| TTT TTC CCT TTC GGC AAC CCC ATA CAC AAC AAC ACG ATG ATT ATG CGG<br>Phe Phe Pro Phe Gly Asn Pro Ile His Asn Asn Thr Met Ile Met Arg<br>                  165                    170                    175 | 972 |
| CGC AGC GTC ATT GAC GGC GGT TTG CGT TAC GAC ACC GAG CGG GAT TGG<br>Arg Ser Val Ile Asp Gly Gly Leu Arg Tyr Asp Thr Glu Arg Asp Trp<br>                  180                    185                    190 | 1020 |
| GCG GAA GAT TAC CAA TTT TGG TAC GAT GTC AGC AAA TTG GGC AGG CTG<br>Ala Glu Asp Tyr Gln Phe Trp Tyr Asp Val Ser Lys Leu Gly Arg Leu<br>              195                    200                    205 | 1068 |
| GCT TAT TAT CCC GAA GCC TTG GTC AAA TAC CGC CTT CAC GCC AAT CAG<br>Ala Tyr Tyr Pro Glu Ala Leu Val Lys Tyr Arg Leu His Ala Asn Gln<br>    210                     215                    220 | 1116 |
| GTT TCA TCC AAA CAC AGC GTC CGC CAA CAC GAA ATC GCG CAA GGC ATC<br>Val Ser Ser Lys His Ser Val Arg Gln His Glu Ile Ala Gln Gly Ile<br>225                     230                    235                  240 | 1164 |
| CAA AAA ACC GCC AGA AAC GAT TTT TTG CAG TCT ATG GGT TTT AAA ACC<br>Gln Lys Thr Ala Arg Asn Asp Phe Leu Gln Ser Met Gly Phe Lys Thr<br>                  245                    250                    255 | 1212 |
| CGG TTC GAC AGC CTA GAA TAC CGC CAA ACA AAA GCA GCG GCG TAT GAA<br>Arg Phe Asp Ser Leu Glu Tyr Arg Gln Thr Lys Ala Ala Ala Tyr Glu<br>                260                    265                    270 | 1260 |
| CTG CCG GAG AAG GAT TTG CCG GAA GAA GAT TTT GAA CGC GCC CGC CGG<br>Leu Pro Glu Lys Asp Leu Pro Glu Glu Asp Phe Glu Arg Ala Arg Arg<br>         275                    280                    285 | 1308 |
| TTT TTG TAC CAA TGC TTC AAA CGG ACG GAC ACG CCG CCC TCC GGC GCG<br>Phe Leu Tyr Gln Cys Phe Lys Arg Thr Asp Thr Pro Pro Ser Gly Ala<br>        290                    295                    300 | 1356 |
| TGG CTG GAT TTC GCG GCA GAC GGC AGG ATG AGG CGG CTG TTT ACC TTG<br>Trp Leu Asp Phe Ala Ala Asp Gly Arg Met Arg Arg Leu Phe Thr Leu<br>305                     310                    315                  320 | 1404 |

```
AGG CAA TAC TTC GGC ATT TTG TAC CGG CTG ATT AAA AAC CGC CGG CAG      1452
Arg Gln Tyr Phe Gly Ile Leu Tyr Arg Leu Ile Lys Asn Arg Arg Gln
                325                 330                 335

GCG CGG TCG GAT TCG GCA GGG AAA GAA CAG GAG ATT TAATGCAAAA           1498
Ala Arg Ser Asp Ser Ala Gly Lys Glu Gln Glu Ile
        340                 345

CCACGTTATC AGCTTGGCTT CCGCCGCAGA ACGCAGGGCG CACATTGCCG CAACCTTCGG    1558
CAGTCGCGGC ATCCCGTTCC AGTTTTTCGA CGCACTGATG CCGTCTGAAA GGCTGGAACG    1618
GGCAATGGCG GAACTCGTCC CCGGCTTGTC GGCGCACCCC TATTTGAGCG GAGTGGAAAA    1678
AGCCTGCTTT ATGAGCCACG CCGTATTGTG GAACAGGCA TTGGACGAAG GCGTACCGTA     1738
TATCGCCGTA TTTGAAGATG ATGTCTTACT CGGCGAAGGC GCGGAGCAGT TCCTTGCCGA    1798
AGATACTTGG CTGCAAGAAC GCTTTGACCC CGATTCCGCC TTTGTCGTCC GCTTGGAAAC    1858
GATGTTTATG CACGTCCTGA CCTCGCCCTC CGGCGTGGCG GACTACGGCG GGCGCGCCTT    1918
TCCGCTTTTG GAAAGCGAAC ACTGCGGGAC GGCGGGCTAT ATTATTTCCC GAAAGGCGAT    1978
GCGTTTTTTC TTGGACAGGT TTGCCGTTTT GCCGCCCGAA CGCCTGCACC CTGTCGATTT    2038
GATGATGTTC GGCAACCCTG ACGACAGGGA AGGAATGCCG GTTTGCCAGC TCAATCCCGC    2098
CTTGTGCGCC CAAGAGCTGC ATTATGCCAA GTTTCACGAC CAAAACAGCG CATTGGGCAG    2158
CCTGATCGAA CATGACCGCC GCCTGAACCG CAAACAGCAA TGGCGCGATT CCCCCGCCAA    2218
CACATTCAAA CACCGCCTGA TCCGCGCCTT GACCAAAATC GGCAGGGAAA GGGAAAAACG    2278
CCGGCAAAGG CGCGAACAGT TAATCGGCAA GATTATTGTG CCTTTCCAAT AAAAGGAGAA    2338

AAG ATG GAC ATC GTA TTT GCG GCA GAC GAC AAC TAT GCC GCC TAC CTT     2386
    Met Asp Ile Val Phe Ala Ala Asp Asp Asn Tyr Ala Ala Tyr Leu
    1               5                  10                  15

TGC GTT GCG GCA AAA AGC GTG GAA GCG GCC CAT CCC GAT ACG GAA ATC     2434
Cys Val Ala Ala Lys Ser Val Glu Ala Ala His Pro Asp Thr Glu Ile
                20                  25                  30

AGG TTC CAC GTC CTC GAT GCC GGC ATC AGT GAG GAA AAC CGG GCG GCG     2482
Arg Phe His Val Leu Asp Ala Gly Ile Ser Glu Glu Asn Arg Ala Ala
            35                  40                  45

GTT GCC GCC AAT TTG CGG GGG GGG GGT AAT ATC CGC TTT ATA GAC GTA     2530
Val Ala Ala Asn Leu Arg Gly Gly Gly Asn Ile Arg Phe Ile Asp Val
        50                  55                  60

AAC CCC GAA GAT TTC GCC GGC TTC CCC TTA AAC ATC AGG CAC ATT TCC     2578
Asn Pro Glu Asp Phe Ala Gly Phe Pro Leu Asn Ile Arg His Ile Ser
    65                  70                  75

ATT ACG ACT TAT GCC CGC CTG AAA TTG GGC GAA TAC ATT GCC GAT TGC     2626
Ile Thr Thr Tyr Ala Arg Leu Lys Leu Gly Glu Tyr Ile Ala Asp Cys
80                  85                  90                  95

GAC AAA GTC CTG TAT CTG GAT ACG GAC GTA TTG GTC AGG GAC GGC CTG     2674
Asp Lys Val Leu Tyr Leu Asp Thr Asp Val Leu Val Arg Asp Gly Leu
                100                 105                 110

AAG CCC TTA TGG GAT ACC GAT TTG GGC GGT AAC TGG GTC GGC GCG TGC     2722
Lys Pro Leu Trp Asp Thr Asp Leu Gly Gly Asn Trp Val Gly Ala Cys
            115                 120                 125

ATC GAT TTG TTT GTC GAA AGG CAG GAA GGA TAC AAA CAA AAA ATC GGT     2770
Ile Asp Leu Phe Val Glu Arg Gln Glu Gly Tyr Lys Gln Lys Ile Gly
        130                 135                 140

ATG GCG GAC GGA GAA TAT TAT TTC AAT GCC GGC GTA TTG CTG ATC AAC     2818
Met Ala Asp Gly Glu Tyr Tyr Phe Asn Ala Gly Val Leu Leu Ile Asn
    145                 150                 155

CTG AAA AAG TGG CGG CGG CAC GAT ATT TTC AAA ATG TCC TGC GAA TGG     2866
Leu Lys Lys Trp Arg Arg His Asp Ile Phe Lys Met Ser Cys Glu Trp
160                 165                 170                 175
```

| | | |
|---|---|---|
| GTG GAA CAA TAC AAG GAC GTG ATG CAA TAT CAG GAT CAG GAC ATT TTG<br>Val Glu Gln Tyr Lys Asp Val Met Gln Tyr Gln Asp Gln Asp Ile Leu<br>180 185 190 | 2914 |
| AAC GGG CTG TTT AAA GGC GGG GTG TGT TAT GCG AAC AGC CGT TTC AAC<br>Asn Gly Leu Phe Lys Gly Gly Val Cys Tyr Ala Asn Ser Arg Phe Asn<br>195 200 205 | 2962 |
| TTT ATG CCG ACC AAT TAT GCC TTT ATG GCG AAC GGG TTT GCG TCC CGC<br>Phe Met Pro Thr Asn Tyr Ala Phe Met Ala Asn Gly Phe Ala Ser Arg<br>210 215 220 | 3010 |
| CAT ACC GAC CCG CTT TAC CTC GAC CGT ACC AAT ACG GCG ATG CCC GTC<br>His Thr Asp Pro Leu Tyr Leu Asp Arg Thr Asn Thr Ala Met Pro Val<br>225 230 235 | 3058 |
| GCC GTC AGC CAT TAT TGC GGC TCG GCA AAG CCG TGG CAC AGG GAC TGC<br>Ala Val Ser His Tyr Cys Gly Ser Ala Lys Pro Trp His Arg Asp Cys<br>240 245 250 255 | 3106 |
| ACC GTT TGG GGT GCG GAA CGT TTC ACA GAG TTG GCC GGC AGC CTG ACG<br>Thr Val Trp Gly Ala Glu Arg Phe Thr Glu Leu Ala Gly Ser Leu Thr<br>260 265 270 | 3154 |
| ACC GTT CCC GAA GAA TGG CGC GGC AAA CTT GCC GTC CCG CCG ACA AAG<br>Thr Val Pro Glu Glu Trp Arg Gly Lys Leu Ala Val Pro Pro Thr Lys<br>275 280 285 | 3202 |
| TGT ATG CTT CAA AGA TGG CGC AAA AAG CTG TCT GCC AGA TTC TTA CGC<br>Cys Met Leu Gln Arg Trp Arg Lys Lys Leu Ser Ala Arg Phe Leu Arg<br>290 295 300 | 3250 |
| AAG ATT TAT TGACGGGCA GGCCGTCTGA AGCCTTCAGA CGGCATCGGA<br>Lys Ile Tyr<br>305 | 3299 |
| CGTATCGGAA AGGAGAAACG GA TTG CAG CCT TTA GTC AGC GTA TTG ATT TGC<br>Met Gln Pro Leu Val Ser Val Leu Ile Cys<br>1 5 10 | 3351 |
| GCC TAC AAC GCA GAA AAA TAT TTT GCC CAA TCA TTG GCC GCC GTA GTG<br>Ala Tyr Asn Ala Glu Lys Tyr Phe Ala Gln Ser Leu Ala Ala Val Val<br>15 20 25 | 3399 |
| GGG CAG ACT TGG CGC AAC TTG GAT ATT TTG ATT GTC GAT GAC GGC TCG<br>Gly Gln Thr Trp Arg Asn Leu Asp Ile Leu Ile Val Asp Asp Gly Ser<br>30 35 40 | 3447 |
| ACG GAC GGC ACG CCC GCC ATT GCC CGG CAT TTC CAA GAA CAG GAC GGC<br>Thr Asp Gly Thr Pro Ala Ile Ala Arg His Phe Gln Glu Gln Asp Gly<br>45 50 55 | 3495 |
| AGG ATC AGG ATA ATT TCC AAT CCC CGC AAT TTG GGC TTT ATC GCC TCT<br>Arg Ile Arg Ile Ile Ser Asn Pro Arg Asn Leu Gly Phe Ile Ala Ser<br>60 65 70 | 3543 |
| TTA AAC ATC GGG CTG GAC GAA TTG GCA AAG TCG GGG GGG GGG GAA TAT<br>Leu Asn Ile Gly Leu Asp Glu Leu Ala Lys Ser Gly Gly Gly Glu Tyr<br>75 80 85 90 | 3591 |
| ATT GCG CGC ACC GAT GCC GAC GAT ATT GCC TCC CCC GGC TGG ATT GAG<br>Ile Ala Arg Thr Asp Ala Asp Asp Ile Ala Ser Pro Gly Trp Ile Glu<br>95 100 105 | 3639 |
| AAA ATC GTG GGC GAG ATG GAA AAA GAC CGC AGC ATC ATT GCG ATG GGC<br>Lys Ile Val Gly Glu Met Glu Lys Asp Arg Ser Ile Ile Ala Met Gly<br>110 115 120 | 3687 |
| GCG TGG TTG GAA GTT TTG TCG GAA GAA AAC AAT AAA AGC GTG CTT GCC<br>Ala Trp Leu Glu Val Leu Ser Glu Glu Asn Asn Lys Ser Val Leu Ala<br>125 130 135 | 3735 |
| GCC ATT GCC CGA AAC GGC GCA ATT TGG GAC AAA CCG ACC CGG CAT GAA<br>Ala Ile Ala Arg Asn Gly Ala Ile Trp Asp Lys Pro Thr Arg His Glu<br>140 145 150 | 3783 |
| GAC ATT GTC GCC GTT TTC CCT TTC GGC AAC CCC ATA CAC AAC AAC ACG<br>Asp Ile Val Ala Val Phe Pro Phe Gly Asn Pro Ile His Asn Asn Thr<br>155 160 165 170 | 3831 |

-continued

| | |
|---|---|
| ATG ATT ATG AGG CGC AGC GTC ATT GAC GGC GGT TTG CGG TTC GAT CCA<br>Met Ile Met Arg Arg Ser Val Ile Asp Gly Gly Leu Arg Phe Asp Pro<br>                           175                      180                        185 | 3879 |
| GCC TAT ATC CAC GCC GAA GAC TAT AAG TTT TGG TAC GAA GCC GGC AAA<br>Ala Tyr Ile His Ala Glu Asp Tyr Lys Phe Trp Tyr Glu Ala Gly Lys<br>                         190                       195                        200 | 3927 |
| CTG GGC AGG CTG GCT TAT TAT CCC GAA GCC TTG GTC AAA TAC CGC TTC<br>Leu Gly Arg Leu Ala Tyr Tyr Pro Glu Ala Leu Val Lys Tyr Arg Phe<br>               205                       210                       215 | 3975 |
| CAT CAA GAC CAG ACT TCT TCC AAA TAC AAC CTG CAA CAG CGC AGG ACG<br>His Gln Asp Gln Thr Ser Ser Lys Tyr Asn Leu Gln Gln Arg Arg Thr<br>220                        225                        230 | 4023 |
| GCG TGG AAA ATC AAA GAA GAA ATC AGG GCG GGG TAT TGG AAG GCG GCA<br>Ala Trp Lys Ile Lys Glu Glu Ile Arg Ala Gly Tyr Trp Lys Ala Ala<br>235                        240                        245                        250 | 4071 |
| GGC ATA GCC GTC GGG GCG GAC TGC CTG AAT TAC GGG CTT TTG AAA TCA<br>Gly Ile Ala Val Gly Ala Asp Cys Leu Asn Tyr Gly Leu Leu Lys Ser<br>                         255                       260                       265 | 4119 |
| ACG GCA TAT GCG TTG TAC GAA AAA GCC TTG TCC GGA CAG GAT ATC GGA<br>Thr Ala Tyr Ala Leu Tyr Glu Lys Ala Leu Ser Gly Gln Asp Ile Gly<br>               270                       275                       280 | 4167 |
| TGC CTC CGC CTG TTC CTG TAC GAA TAT TTC TTG TCG TTG GAA AAG TAT<br>Cys Leu Arg Leu Phe Leu Tyr Glu Tyr Phe Leu Ser Leu Glu Lys Tyr<br>             285                       290                       295 | 4215 |
| TCT TTG ACC GAT TTG CTG GAT TTC TTG ACA GAC CGC GTG ATG AGG AAG<br>Ser Leu Thr Asp Leu Leu Asp Phe Leu Thr Asp Arg Val Met Arg Lys<br>300                        305                        310 | 4263 |
| CTG TTT GCC GCA CCG CAA TAT AGG AAA ATC CTG AAA AAA ATG TTA CGC<br>Leu Phe Ala Ala Pro Gln Tyr Arg Lys Ile Leu Lys Lys Met Leu Arg<br>315                        320                        325                        330 | 4311 |
| CCT TGG AAA TAC CGC AGC TAT TGAAACCGAA CAGGATAAAT C ATG CAA AAC<br>Pro Trp Lys Tyr Arg Ser Tyr                                             Met Gln Asn<br>               335                                                               1 | 4362 |
| CAC GTT ATC AGC TTG GCT TCC GCC GCA GAG CGC AGG GCG CAC ATT GCC<br>His Val Ile Ser Leu Ala Ser Ala Ala Glu Arg Arg Ala His Ile Ala<br>      5                        10                         15 | 4410 |
| GAT ACC TTC GGC AGT CGC GGC ATC CCG TTC CAG TTT TTC GAC GCA CTG<br>Asp Thr Phe Gly Ser Arg Gly Ile Pro Phe Gln Phe Phe Asp Ala Leu<br>20                        25                        30                        35 | 4458 |
| ATG CCG TCT GAA AGG CTG GAA CAG GCG ATG GCG GAA CTC GTC CCC GGC<br>Met Pro Ser Glu Arg Leu Glu Gln Ala Met Ala Glu Leu Val Pro Gly<br>               40                       45                        50 | 4506 |
| TTG TCG GCG CAC CCC TAT TTG AGC GGA GTG GAA AAA GCC TGC TTT ATG<br>Leu Ser Ala His Pro Tyr Leu Ser Gly Val Glu Lys Ala Cys Phe Met<br>             55                       60                        65 | 4554 |
| AGC CAC GCC GTA TTG TGG GAA CAG GCG TTG GAT GAA GGT CTG CCG TAT<br>Ser His Ala Val Leu Trp Glu Gln Ala Leu Asp Glu Gly Leu Pro Tyr<br>      70                       75                       80 | 4602 |
| ATC GCC GTA TTT GAG GAC GAC GTT TTA CTC GGC GAA GGC GCG GAG CAG<br>Ile Ala Val Phe Glu Asp Asp Val Leu Leu Gly Glu Gly Ala Glu Gln<br>85                        90                        95 | 4650 |
| TTC CTT GCC GAA GAT ACT TGG TTG GAA GAG CGT TTT GAC AAG GAT TCC<br>Phe Leu Ala Glu Asp Thr Trp Leu Glu Glu Arg Phe Asp Lys Asp Ser<br>100                       105                       110                       115 | 4698 |
| GCC TTT ATC GTC CGT TTG GAA ACG ATG TTT GCG AAA GTT ATT GTC AGA<br>Ala Phe Ile Val Arg Leu Glu Thr Met Phe Ala Lys Val Ile Val Arg<br>                         120                       125                       130 | 4746 |
| CCG GAT AAA GTC CTG AAT TAT GAA AAC CGG TCA TTT CCT TTG CTG GAG<br>Pro Asp Lys Val Leu Asn Tyr Glu Asn Arg Ser Phe Pro Leu Leu Glu<br>                         135                       140                       145 | 4794 |

```
AGC GAA CAT TGT GGG ACG GCT GGC TAT ATC ATT TCG CGT GAG GCG ATG      4842
Ser Glu His Cys Gly Thr Ala Gly Tyr Ile Ile Ser Arg Glu Ala Met
        150                 155                 160

CGG TTT TTC TTG GAC AGG TTT GCC GTT TTG CCG CCA GAG CGG ATT AAA      4890
Arg Phe Phe Leu Asp Arg Phe Ala Val Leu Pro Pro Glu Arg Ile Lys
165                 170                 175

GCG GTA GAT TTG ATG ATG TTT ACT TAT TTC TTT GAT AAG GAG GGG ATG      4938
Ala Val Asp Leu Met Met Phe Thr Tyr Phe Phe Asp Lys Glu Gly Met
180                 185                 190                 195

CCT GTT TAT CAG GTT AGT CCC GCC TTA TGT ACC CAA GAA TTG CAT TAT      4986
Pro Val Tyr Gln Val Ser Pro Ala Leu Cys Thr Gln Glu Leu His Tyr
                200                 205                 210

GCC AAG TTT CTC AGT CAA AAC AGT ATG TTG GGT AGC GAT TTG GAA AAA      5034
Ala Lys Phe Leu Ser Gln Asn Ser Met Leu Gly Ser Asp Leu Glu Lys
            215                 220                 225

GAT AGG GAA CAA GGA AGA AGA CAC CGC CGT TCG TTG AAG GTG ATG TTT      5082
Asp Arg Glu Gln Gly Arg Arg His Arg Arg Ser Leu Lys Val Met Phe
        230                 235                 240

GAC TTG AAG CGT GCT TTG GGT AAA TTC GGT AGG GAA AAG AAG AAA AGA      5130
Asp Leu Lys Arg Ala Leu Gly Lys Phe Gly Arg Glu Lys Lys Lys Arg
    245                 250                 255

ATG GAG CGT CAA AGG CAG GCG GAG CTT GAG AAA GTT TAC GGC AGG CGG      5178
Met Glu Arg Gln Arg Gln Ala Glu Leu Glu Lys Val Tyr Gly Arg Arg
260                 265                 270                 275

GTC ATA TTG TTC AAA TAGTTTGTGT AAAATATAGG GGATTAAAAT CAGAAATGGA      5233
Val Ile Leu Phe Lys
                280

CACACTGTCA TTCCCGCGCA GGCGGGAATC TAGGTCTTTA AACTTCGGTT TTTTCCGATA    5293

AATTCTTGCC GCATTAAAAT TCCAGATTCC CGCTTTCGCG GGGATGACGG CGGGGGGATT    5353

GTTGCTTTTT CGGATAAAAT CCCGTGTTTT TTCATCTGCT AGGTAAAATC GCCCCAAAGC    5413

GTCTGCATCG CGGCGATGGC GGCGAGTGGG GCGGTTTCTG TGCGTAAAAT CCGTTTTCCG    5473

AGTGTAACCG CCTGAAAGCC GGCTTCAAAT GCCTGTTGTT CTTCCTGTTC TGTCCAGCCG    5533

CCTTCGGGCC CGACCATAAA GACGATTGCG CCGGACGGGT GGCGGATGTC GCCGAGTTTG    5593

CAGGCGCGGT TGATGCTCAT AATCAGCTTG GTGTTTTCAG ACGGCATTTT GTCGAGTGCT    5653

TCACGGTAGC CGATGATGGG CAGTACGGGG GGAACGGTGT TCCTGCCGCT TGTTCGCAC     5713

GCGGAGATGA CGATTTCCTG CCAGCGTGCG AGGCGTTTGG CGGCGCGTTC TCCGTCGAGG    5773

CGGACGATGC AGCGTTCGCT GATGACGGGC TGTATGGCGG TTACGCCGAG TTCGACGCTT    5833

TTTTGCAGGG TGAAATCCAT GCGATC                                         5859
```

(2) INFORMATION FOR SEQ ID NO:2:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Gln Ala Val Ala Val Phe Lys Gln Leu Pro Glu Ala Ala Leu
1               5                   10                  15

Ala Ala Ala Asn Lys Arg Val Gln Asn Leu Leu Lys Lys Ala Asp Ala
            20                  25                  30

Ala Leu Gly Glu Val Asn Glu Ser Leu Leu Gln Gln Asp Glu Glu Lys
        35                  40                  45

Ala Leu Tyr Ala Ala Ala Gln Gly Leu Gln Pro Lys Ile Ala Ala Ala
```

```
                50                    55                    60
Val Ala Glu Gly Asn Phe Arg Thr Ala Leu Ser Glu Leu Ala Ser Val
 65                  70                   75                  80

Lys Pro Gln Val Asp Ala Phe Phe Asp Gly Val Met Val Met Ala Glu
                     85                   90                  95

Asp Ala Ala Val Lys Gln Asn Arg Leu Asn Leu Leu Asn Arg Leu Ala
                    100                  105                 110

Glu Gln Met Asn Ala Val Ala Asp Ile Ala Leu Leu Gly Glu
                    115                  120                 125

(2) INFORMATION FOR SEQ ID NO:3:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:3:

Met Gln Pro Leu Val Ser Val Leu Ile Cys Ala Tyr Asn Val Glu Lys
  1                   5                   10                  15

Tyr Phe Ala Gln Ser Leu Ala Ala Val Val Asn Gln Thr Trp Arg Asn
                     20                   25                  30

Leu Asp Ile Leu Ile Val Asp Asp Gly Ser Thr Asp Gly Thr Leu Ala
                     35                   40                  45

Ile Ala Lys Asp Phe Gln Lys Arg Asp Ser Arg Ile Lys Ile Leu Ala
 50                  55                   60

Gln Ala Gln Asn Ser Gly Leu Ile Pro Ser Leu Asn Ile Gly Leu Asp
 65                  70                   75                  80

Glu Leu Ala Lys Ser Gly Gly Gly Gly Glu Tyr Ile Ala Arg Thr
                     85                   90                  95

Asp Ala Asp Asp Ile Ala Ser Pro Gly Trp Ile Glu Lys Ile Val Gly
                    100                  105                 110

Glu Met Glu Lys Asp Arg Ser Ile Ile Ala Met Gly Ala Trp Leu Glu
                    115                  120                 125

Val Leu Ser Glu Glu Lys Asp Gly Asn Arg Leu Ala Arg His His Lys
130                  135                  140

His Gly Lys Ile Trp Lys Lys Pro Thr Arg His Glu Asp Ile Ala Ala
145                  150                  155                 160

Phe Phe Pro Phe Gly Asn Pro Ile His Asn Asn Thr Met Ile Met Arg
                    165                  170                 175

Arg Ser Val Ile Asp Gly Gly Leu Arg Tyr Asp Thr Glu Arg Asp Trp
                    180                  185                 190

Ala Glu Asp Tyr Gln Phe Trp Tyr Asp Val Ser Lys Leu Gly Arg Leu
                    195                  200                 205

Ala Tyr Tyr Pro Glu Ala Leu Val Lys Tyr Arg Leu His Ala Asn Gln
                    210                  215                 220

Val Ser Ser Lys His Ser Val Arg Gln His Glu Ile Ala Gln Gly Ile
225                  230                  235                 240

Gln Lys Thr Ala Arg Asn Asp Phe Leu Gln Ser Met Gly Phe Lys Thr
                    245                  250                 255

Arg Phe Asp Ser Leu Glu Tyr Arg Gln Thr Lys Ala Ala Ala Tyr Glu
                    260                  265                 270

Leu Pro Glu Lys Asp Leu Pro Glu Asp Phe Glu Arg Ala Arg Arg
                    275                  280                 285
```

```
Phe Leu Tyr Gln Cys Phe Lys Arg Thr Asp Thr Pro Pro Ser Gly Ala
    290                 295                 300

Trp Leu Asp Phe Ala Ala Asp Gly Arg Met Arg Arg Leu Phe Thr Leu
305                 310                 315                 320

Arg Gln Tyr Phe Gly Ile Leu Tyr Arg Leu Ile Lys Asn Arg Arg Gln
                325                 330                 335

Ala Arg Ser Asp Ser Ala Gly Lys Glu Gln Glu Ile
            340                 345
```

(2) INFORMATION FOR SEQ ID NO:4:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Ile Val Phe Ala Ala Asp Asp Asn Tyr Ala Ala Tyr Leu Cys
1               5                   10                  15

Val Ala Ala Lys Ser Val Glu Ala Ala His Pro Asp Thr Glu Ile Arg
                20                  25                  30

Phe His Val Leu Asp Ala Gly Ile Ser Glu Glu Asn Arg Ala Ala Val
            35                  40                  45

Ala Ala Asn Leu Arg Gly Gly Gly Asn Ile Arg Phe Ile Asp Val Asn
        50                  55                  60

Pro Glu Asp Phe Ala Gly Phe Pro Leu Asn Ile Arg His Ile Ser Ile
65                  70                  75                  80

Thr Thr Tyr Ala Arg Leu Lys Leu Gly Glu Tyr Ile Ala Asp Cys Asp
                85                  90                  95

Lys Val Leu Tyr Leu Asp Thr Asp Val Leu Val Arg Asp Gly Leu Lys
                100                 105                 110

Pro Leu Trp Asp Thr Asp Leu Gly Gly Asn Trp Val Gly Ala Cys Ile
            115                 120                 125

Asp Leu Phe Val Glu Arg Gln Glu Gly Tyr Lys Gln Lys Ile Gly Met
        130                 135                 140

Ala Asp Gly Glu Tyr Tyr Phe Asn Ala Gly Val Leu Leu Ile Asn Leu
145                 150                 155                 160

Lys Lys Trp Arg Arg His Asp Ile Phe Lys Met Ser Cys Glu Trp Val
                165                 170                 175

Glu Gln Tyr Lys Asp Val Met Gln Tyr Gln Asp Gln Asp Ile Leu Asn
                180                 185                 190

Gly Leu Phe Lys Gly Gly Val Cys Tyr Ala Asn Ser Arg Phe Asn Phe
            195                 200                 205

Met Pro Thr Asn Tyr Ala Phe Met Ala Asn Gly Phe Ala Ser Arg His
        210                 215                 220

Thr Asp Pro Leu Tyr Leu Asp Arg Thr Asn Thr Ala Met Pro Val Ala
225                 230                 235                 240

Val Ser His Tyr Cys Gly Ser Ala Lys Pro Trp His Arg Asp Cys Thr
                245                 250                 255

Val Trp Gly Ala Glu Arg Phe Thr Glu Leu Ala Gly Ser Leu Thr Thr
            260                 265                 270

Val Pro Glu Glu Trp Arg Gly Lys Leu Ala Val Pro Pro Thr Lys Cys
        275                 280                 285

Met Leu Gln Arg Trp Arg Lys Lys Leu Ser Ala Arg Phe Leu Arg Lys
290                 295                 300
```

Ile Tyr
305

(2) INFORMATION FOR SEQ ID NO:5:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:5:

```
Met Gln Pro Leu Val Ser Val Leu Ile Cys Ala Tyr Asn Ala Glu Lys
 1               5                  10                  15

Tyr Phe Ala Gln Ser Leu Ala Ala Val Val Gly Gln Thr Trp Arg Asn
                20                  25                  30

Leu Asp Ile Leu Ile Val Asp Asp Gly Ser Thr Asp Gly Thr Pro Ala
            35                  40                  45

Ile Ala Arg His Phe Gln Glu Gln Asp Gly Arg Ile Arg Ile Ile Ser
        50                  55                  60

Asn Pro Arg Asn Leu Gly Phe Ile Ala Ser Leu Asn Ile Gly Leu Asp
 65                  70                  75                  80

Glu Leu Ala Lys Ser Gly Gly Glu Tyr Ile Ala Arg Thr Asp Ala
                85                  90                  95

Asp Asp Ile Ala Ser Pro Gly Trp Ile Glu Lys Ile Val Gly Glu Met
            100                 105                 110

Glu Lys Asp Arg Ser Ile Ile Ala Met Gly Ala Trp Leu Glu Val Leu
        115                 120                 125

Ser Glu Glu Asn Asn Lys Ser Val Leu Ala Ala Ile Ala Arg Asn Gly
130                 135                 140

Ala Ile Trp Asp Lys Pro Thr Arg His Glu Asp Ile Val Ala Val Phe
145                 150                 155                 160

Pro Phe Gly Asn Pro Ile His Asn Asn Thr Met Ile Met Arg Arg Ser
                165                 170                 175

Val Ile Asp Gly Gly Leu Arg Phe Asp Pro Ala Tyr Ile His Ala Glu
            180                 185                 190

Asp Tyr Lys Phe Trp Tyr Glu Ala Gly Lys Leu Gly Arg Leu Ala Tyr
        195                 200                 205

Tyr Pro Glu Ala Leu Val Lys Tyr Arg Phe His Gln Asp Gln Thr Ser
210                 215                 220

Ser Lys Tyr Asn Leu Gln Gln Arg Thr Ala Trp Lys Ile Lys Glu
225                 230                 235                 240

Glu Ile Arg Ala Gly Tyr Trp Lys Ala Ala Gly Ile Ala Val Gly Ala
                245                 250                 255

Asp Cys Leu Asn Tyr Gly Leu Leu Lys Ser Thr Ala Tyr Ala Leu Tyr
            260                 265                 270

Glu Lys Ala Leu Ser Gly Gln Asp Ile Gly Cys Leu Arg Leu Phe Leu
        275                 280                 285

Tyr Glu Tyr Phe Leu Ser Leu Glu Lys Tyr Ser Leu Thr Asp Leu Leu
290                 295                 300

Asp Phe Leu Thr Asp Arg Val Met Arg Lys Leu Phe Ala Ala Pro Gln
305                 310                 315                 320

Tyr Arg Lys Ile Leu Lys Lys Met Leu Arg Pro Trp Lys Tyr Arg Ser
                325                 330                 335

Tyr
```

(2) INFORMATION FOR SEQ ID NO:6:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gln Asn His Val Ile Ser Leu Ala Ser Ala Ala Glu Arg Arg Ala
 1               5                  10                  15

His Ile Ala Asp Thr Phe Gly Ser Arg Gly Ile Pro Phe Gln Phe Phe
             20                  25                  30

Asp Ala Leu Met Pro Ser Glu Arg Leu Glu Gln Ala Met Ala Glu Leu
         35                  40                  45

Val Pro Gly Leu Ser Ala His Pro Tyr Leu Ser Gly Val Glu Lys Ala
     50                  55                  60

Cys Phe Met Ser His Ala Val Leu Trp Glu Gln Ala Leu Asp Glu Gly
 65                  70                  75                  80

Leu Pro Tyr Ile Ala Val Phe Glu Asp Asp Val Leu Leu Gly Glu Gly
             85                  90                  95

Ala Glu Gln Phe Leu Ala Glu Asp Thr Trp Leu Glu Glu Arg Phe Asp
        100                 105                 110

Lys Asp Ser Ala Phe Ile Val Arg Leu Glu Thr Met Phe Ala Lys Val
    115                 120                 125

Ile Val Arg Pro Asp Lys Val Leu Asn Tyr Glu Asn Arg Ser Phe Pro
130                 135                 140

Leu Leu Glu Ser Glu His Cys Gly Thr Ala Gly Tyr Ile Ile Ser Arg
145                 150                 155                 160

Glu Ala Met Arg Phe Phe Leu Asp Arg Phe Ala Val Leu Pro Pro Glu
                165                 170                 175

Arg Ile Lys Ala Val Asp Leu Met Met Phe Thr Tyr Phe Phe Asp Lys
            180                 185                 190

Glu Gly Met Pro Val Tyr Gln Val Ser Pro Ala Leu Cys Thr Gln Glu
        195                 200                 205

Leu His Tyr Ala Lys Phe Leu Ser Gln Asn Ser Met Leu Gly Ser Asp
    210                 215                 220

Leu Glu Lys Asp Arg Glu Gln Gly Arg His Arg Arg Ser Leu Lys
225                 230                 235                 240

Val Met Phe Asp Leu Lys Arg Ala Leu Gly Lys Phe Gly Arg Glu Lys
                245                 250                 255

Lys Lys Arg Met Glu Arg Gln Arg Gln Ala Glu Leu Glu Lys Val Tyr
            260                 265                 270

Gly Arg Arg Val Ile Leu Phe Lys
        275                 280
```

(2) INFORMATION FOR SEQ ID NO:7:

(i) SEQUENCE CHARACTERISTICS:
        (A) LENGTH: 5859 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO

-continued (iv) ANTI-SENSE: NO (vi) ORIGINAL SOURCE:
    (A) ORGANISM: Neisseria gonorrheae
    (B) STRAIN: F62

(ix) FEATURE:
    (A) NAME/KEY: CDS
    (B) LOCATION: 1491..2330
    (D) OTHER INFORMATION: lgtB (xi) SEQUENCE DESCRIPTION: SEQ ID NO:7:

```
CTGCAGGCCG TCGCCGTATT CAAACAACTG CCCGAAGCCG CCGCGCTCGC CGCCGCCAAC      60

AAACGCGTGC AAAACCTGCT GAAAAAGCC GATGCCGCGT TGGGCGAAGT CAATGAAAGC      120

CTGCTGCAAC AGGACGAAGA AAAAGCCCTG TACGCTGCCG CGCAAGGTTT GCAGCCGAAA      180

ATTGCCGCCG CCGTCGCCGA AGGCAATTTC CGAACCGCCT TGTCCGAACT GGCTTCCGTC      240

AAGCCGCAGG TTGATGCCTT CTTCGACGGC GTGATGGTGA TGGCGGAAGA TGCCGCCGTA      300

AAACAAAACC GCCTGAACCT GCTGAACCGC TTGGCAGAGC AGATGAACGC GGTGGCCGAC      360

ATCGCGCTTT TGGGCGAGTA ACCGTTGTAC AGTCCAAATG CCGTCTGAAG CCTTCAGGCG      420

GCATCAAATT ATCGGGAGAG TAAATTGCAG CCTTTAGTCA GCGTATTGAT TTGCGCCTAC      480

AACGTAGAAA AATATTTTGC CCAATCATTA GCCGCCGTCG TGAATCAGAC TTGGCGCAAC      540

TTGGATATTT TGATTGTCGA TGACGGCTCG ACAGACGGCA CACTTGCCAT TGCCAAGGAT      600

TTTCAAAAGC GGGACAGCCG TATCAAAATC CTTGCACAAG CTCAAAATTC CGGCCTGATT      660

CCCTCTTTAA ACATCGGGCT GGACGAATTG GCAAAGTCGG GGGGGGGGGG GGGGGAATAT      720

ATTGCGCGCA CCGATGCCGA CGATATTGCC TCCCCCGGCT GGATTGAGAA AATCGTGGGC      780

GAGATGGAAA AAGACCGCAG CATCATTGCG ATGGGCGCGT GGCTGGAAGT TTTGTCGGAA      840

GAAAAGGACG GCAACCGGCT GGCGCGGCAC CACAAACACG GCAAAATTTG GAAAAAGCCG      900

ACCCGGCACG AAGACATCGC CGCCTTTTTC CCTTTCGGCA ACCCCATACA CAACAACACG      960

ATGATTATGC GGCGCAGCGT CATTGACGGC GGTTTGCGTT ACGACACCGA GCGGGATTGG      1020

GCGGAAGATT ACCAATTTTG GTACGATGTC AGCAAATTGG CAGGCTGGC  TTATTATCCC      1080

GAAGCCTTGG TCAAATACCG CCTTCACGCC AATCAGGTTT CATCCAAACA CAGCGTCCGC      1140

CAACACGAAA TCGCGCAAGG CATCCAAAAA ACCGCCAGAA ACGATTTTTT GCAGTCTATG      1200

GGTTTTAAAA CCCGGTTCGA CAGCCTAGAA TACCGCCAAA CAAAAGCAGC GGCGTATGAA      1260

CTGCCGGAGA AGGATTTGCC GGAAGAAGAT TTTGAACGCG CCCGCCGGTT TTTGTACCAA      1320

TGCTTCAAAC GGACGGACAC GCCGCCCTCC GGCGCGTGGC TGGATTTCGC GGCAGACGGC      1380

AGGATGAGGC GGCTGTTTAC CTTGAGGCAA TACTTCGGCA TTTTGTACCG GCTGATTAAA      1440

AACCGCCGGC AGGCGCGGTC GGATTCGGCA GGGAAAGAAC AGGAGATTTA ATG CAA       1496
                                                         Met Gln
                                                           1

AAC CAC GTT ATC AGC TTG GCT TCC GCC GCA GAA CGC AGG GCG CAC ATT     1544
Asn His Val Ile Ser Leu Ala Ser Ala Ala Glu Arg Arg Ala His Ile
        5                  10                  15

GCC GCA ACC TTC GGC AGT CGC GGC ATC CCG TTC CAG TTT TTC GAC GCA     1592
Ala Ala Thr Phe Gly Ser Arg Gly Ile Pro Phe Gln Phe Phe Asp Ala
            20                  25                  30

CTG ATG CCG TCT GAA AGG CTG GAA CGG GCA ATG GCG GAA CTC GTC CCC     1640
Leu Met Pro Ser Glu Arg Leu Glu Arg Ala Met Ala Glu Leu Val Pro
    35                  40                  45                  50

GGC TTG TCG GCG CAC CCC TAT TTG AGC GGA GTG GAA AAA GCC TGC TTT     1688
Gly Leu Ser Ala His Pro Tyr Leu Ser Gly Val Glu Lys Ala Cys Phe
                55                  60                  65
```

```
ATG AGC CAC GCC GTA TTG TGG GAA CAG GCA TTG GAC GAA GGC GTA CCG      1736
Met Ser His Ala Val Leu Trp Glu Gln Ala Leu Asp Glu Gly Val Pro
            70                  75                  80

TAT ATC GCC GTA TTT GAA GAT GAT GTC TTA CTC GGC GAA GGC GCG GAG      1784
Tyr Ile Ala Val Phe Glu Asp Asp Val Leu Leu Gly Glu Gly Ala Glu
        85                  90                  95

CAG TTC CTT GCC GAA GAT ACT TGG CTG CAA GAA CGC TTT GAC CCC GAT      1832
Gln Phe Leu Ala Glu Asp Thr Trp Leu Gln Glu Arg Phe Asp Pro Asp
    100                 105                 110

TCC GCC TTT GTC GTC CGC TTG GAA ACG ATG TTT ATG CAC GTC CTG ACC      1880
Ser Ala Phe Val Val Arg Leu Glu Thr Met Phe Met His Val Leu Thr
115                 120                 125                 130

TCG CCC TCC GGC GTG GCG GAC TAC GGC GGG CGC GCC TTT CCG CTT TTG      1928
Ser Pro Ser Gly Val Ala Asp Tyr Gly Gly Arg Ala Phe Pro Leu Leu
            135                 140                 145

GAA AGC GAA CAC TGC GGG ACG GCG GGC TAT ATT ATT TCC CGA AAG GCG      1976
Glu Ser Glu His Cys Gly Thr Ala Gly Tyr Ile Ile Ser Arg Lys Ala
        150                 155                 160

ATG CGT TTT TTC TTG GAC AGG TTT GCC GTT TTG CCG CCC GAA CGC CTG      2024
Met Arg Phe Phe Leu Asp Arg Phe Ala Val Leu Pro Pro Glu Arg Leu
    165                 170                 175

CAC CCT GTC GAT TTG ATG ATG TTC GGC AAC CCT GAC GAC AGG GAA GGA      2072
His Pro Val Asp Leu Met Met Phe Gly Asn Pro Asp Asp Arg Glu Gly
180                 185                 190

ATG CCG GTT TGC CAG CTC AAT CCC GCC TTG TGC GCC CAA GAG CTG CAT      2120
Met Pro Val Cys Gln Leu Asn Pro Ala Leu Cys Ala Gln Glu Leu His
195                 200                 205                 210

TAT GCC AAG TTT CAC GAC CAA AAC AGC GCA TTG GGC AGC CTG ATC GAA      2168
Tyr Ala Lys Phe His Asp Gln Asn Ser Ala Leu Gly Ser Leu Ile Glu
            215                 220                 225

CAT GAC CGC CGC CTG AAC CGC AAA CAG CAA TGG CGC GAT TCC CCC GCC      2216
His Asp Arg Arg Leu Asn Arg Lys Gln Gln Trp Arg Asp Ser Pro Ala
        230                 235                 240

AAC ACA TTC AAA CAC CGC CTG ATC CGC GCC TTG ACC AAA ATC GGC AGG      2264
Asn Thr Phe Lys His Arg Leu Ile Arg Ala Leu Thr Lys Ile Gly Arg
    245                 250                 255

GAA AGG GAA AAA CGC CGG CAA AGG CGC GAA CAG TTA ATC GGC AAG ATT      2312
Glu Arg Glu Lys Arg Arg Gln Arg Arg Glu Gln Leu Ile Gly Lys Ile
260                 265                 270

ATT GTG CCT TTC CAA TAAAAGGAGA AAAGATGGAC ATCGTATTTG CGGCAGACGA      2367
Ile Val Pro Phe Gln
275                 280

CAACTATGCC GCCTACCTTT GCGTTGCGGC AAAAAGCGTG GAAGCGGCCC ATCCCGATAC    2427

GGAAATCAGG TTCCACGTCC TCGATGCCGG CATCAGTGAG GAAAACCGGG CGGCGGTTGC    2487

CGCCAATTTG CGGGGGGGGG GTAATATCCG CTTTATAGAC GTAAACCCCG AAGATTTCGC    2547

CGGCTTCCCC TTAAACATCA GGCACATTTC CATTACGACT TATGCCCGCC TGAAATTGGG    2607

CGAATACATT GCCGATTGCG ACAAAGTCCT GTATCTGGAT ACGGACGTAT TGGTCAGGGA    2667

CGGCCTGAAG CCCTTATGGG ATACCGATTT GGGCGGTAAC TGGGTCGGCG CGTGCATCGA    2727

TTTGTTTGTC GAAAGGCAGG AAGGATACAA ACAAAAAATC GGTATGGCGG ACGGAGAATA    2787

TTATTTCAAT GCCGGCGTAT TGCTGATCAA CCTGAAAAAG TGGCGGCGGC ACGATATTTT    2847

CAAAATGTCC TGCGAATGGG TGGAACAATA CAAGGACGTG ATGCAATATC AGGATCAGGA    2907

CATTTTGAAC GGGCTGTTTA AAGGCGGGGT GTGTTATGCG AACAGCCGTT TCAACTTTAT    2967

GCCGACCAAT TATGCCTTTA TGGCGAACGG GTTTGCGTCC CGCCATACCG ACCCGCTTTA    3027

CCTCGACCGT ACCAATACGG CGATGCCCGT CGCCGTCAGC CATTATTGCG GCTCGGCAAA    3087
```

```
GCCGTGGCAC AGGGACTGCA CCGTTTGGGG TGCGGAACGT TTCACAGAGT TGGCCGGCAG    3147

CCTGACGACC GTTCCCGAAG AATGGCGCGG CAAACTTGCC GTCCCGCCGA CAAAGTGTAT    3207

GCTTCAAAGA TGGCGCAAAA AGCTGTCTGC CAGATTCTTA CGCAAGATTT ATTGACGGGG    3267

CAGGCCGTCT GAAGCCTTCA GACGGCATCG GACGTATCGG AAAGGAGAAA CGGATTGCAG    3327

CCTTTAGTCA GCGTATTGAT TTGCGCCTAC AACGCAGAAA AATATTTTGC CCAATCATTG    3387

GCCGCCGTAG TGGGGCAGAC TTGGCGCAAC TTGGATATTT TGATTGTCGA TGACGGCTCG    3447

ACGGACGGCA CGCCCGCCAT TGCCCGGCAT TTCCAAGAAC AGGACGGCAG GATCAGGATA    3507

ATTTCCAATC CCCGCAATTT GGGCTTTATC GCCTCTTTAA ACATCGGGCT GGACGAATTG    3567

GCAAAGTCGG GGGGGGGGA ATATATTGCG CGCACCGATG CCGACGATAT TGCCTCCCCC    3627

GGCTGGATTG AGAAAATCGT GGGCGAGATG GAAAAGACC GCAGCATCAT TGCGATGGGC    3687

GCGTGGTTGG AAGTTTTGTC GGAAGAAAAC AATAAAAGCG TGCTTGCCGC CATTGCCCGA    3747

AACGGCGCAA TTTGGGACAA ACCGACCCGG CATGAAGACA TTGTCGCCGT TTTCCCTTTC    3807

GGCAACCCCA TACACAACAA CACGATGATT ATGAGGCGCA GCGTCATTGA CGGCGGTTTG    3867

CGGTTCGATC CAGCCTATAT CCACGCCGAA GACTATAAGT TTTGGTACGA AGCCGGCAAA    3927

CTGGGCAGGC TGGCTTATTA TCCCGAAGCC TTGGTCAAAT ACCGCTTCCA TCAAGACCAG    3987

ACTTCTTCCA AATACAACCT GCAACAGCGC AGGACGGCGT GGAAAATCAA AGAAGAAATC    4047

AGGGCGGGGT ATTGGAAGGC GGCAGGCATA GCCGTCGGGG CGGACTGCCT GAATTACGGG    4107

CTTTTGAAAT CAACGGCATA TGCGTTGTAC GAAAAAGCCT TGTCCGGACA GGATATCGGA    4167

TGCCTCCGCC TGTTCCTGTA CGAATATTTC TTGTCGTTGG AAAAGTATTC TTGACCGAT    4227

TTGCTGGATT TCTTGACAGA CCGCGTGATG AGGAAGCTGT TGCCGCACC GCAATATAGG    4287

AAAATCCTGA AAAAAATGTT ACGCCCTTGG AAATACCGCA GCTATTGAAA CCGAACAGGA    4347

TAAATCATGC AAAACCACGT TATCAGCTTG GCTTCCGCCG CAGAGCGCAG GGCGCACATT    4407

GCCGATACCT TCGGCAGTCG CGGCATCCCG TTCCAGTTTT TCGACGCACT GATGCCGTCT    4467

GAAAGGCTGG AACAGGCGAT GGCGGAACTC GTCCCCGGCT TGTCGGCGCA CCCCTATTTG    4527

AGCGGAGTGG AAAAAGCCTG CTTTATGAGC CACGCCGTAT TGTGGGAACA GGCGTTGGAT    4587

GAAGGTCTGC CGTATATCGC CGTATTTGAG GACGACGTTT TACTCGGCGA AGGCGCGGAG    4647

CAGTTCCTTG CCGAAGATAC TTGGTTGGAA GAGCGTTTTG ACAAGGATTC CGCCTTTATC    4707

GTCCGTTTGG AAACGATGTT TGCGAAAGTT ATTGTCAGAC CGGATAAAGT CCTGAATTAT    4767

GAAAACCGGT CATTTCCTTT GCTGGAGAGC GAACATTGTG GGACGGCTGG CTATATCATT    4827

TCGCGTGAGG CGATGCGGTT TTTCTTGGAC AGGTTTGCCG TTTTGCCGCC AGAGCGGATT    4887

AAAGCGGTAG ATTTGATGAT GTTTACTTAT TTCTTTGATA AGGAGGGGAT GCCTGTTTAT    4947

CAGGTTAGTC CCGCCTTATG TACCCAAGAA TTGCATTATG CCAAGTTTCT CAGTCAAAAC    5007

AGTATGTTGG GTAGCGATTT GGAAAAAGAT AGGGAACAAG GAAGAAGACA CCGCCGTTCG    5067

TTGAAGGTGA TGTTTGACTT GAAGCGTGCT TTGGGTAAAT TCGGTAGGGA AAAGAAGAAA    5127

AGAATGGAGC GTCAAAGGCA GGCGGAGCTT GAGAAAGTTT ACGGCAGGCG GGTCATATTG    5187

TTCAAATAGT TTGTGTAAAA TATAGGGGAT TAAAATCAGA AATGGACACA CTGTCATTCC    5247

CGCGCAGGCG GGAATCTAGG TCTTTAAACT TCGGTTTTTT CCGATAAATT CTTGCCGCAT    5307

TAAAATTCCA GATTCCCGCT TTCGCGGGGA TGACGGCGGG GGGATTGTTG CTTTTTCGGA    5367

TAAAATCCCG TGTTTTTTCA TCTGCTAGGT AAAATCGCCC CAAAGCGTCT GCATCGCGGC    5427

GATGGCGGCG AGTGGGGCGG TTTCTGTGCG TAAAATCCGT TTTCCGAGTG TAACCGCCTG    5487
```

-continued

```
AAAGCCGGCT TCAAATGCCT GTTGTTCTTC CTGTTCTGTC CAGCCGCCTT CGGGCCCGAC      5547

CATAAAGACG ATTGCGCCGG ACGGGTGGCG GATGTCGCCG AGTTTGCAGG CGCGGTTGAT      5607

GCTCATAATC AGCTTGGTGT TTTCAGACGG CATTTTGTCG AGTGCTTCAC GGTAGCCGAT      5667

GATGGGCAGT ACGGGGGGAA CGGTGTTCCT GCCGCTTTGT TCGCACGCGG AGATGACGAT      5727

TTCCTGCCAG CGTGCGAGGC GTTTGGCGGC GCGTTCTCCG TCGAGGCGGA CGATGCAGCG      5787

TTCGCTGATG ACGGGCTGTA TGGCGGTTAC GCCGAGTTCG ACGCTTTTTT GCAGGGTGAA      5847

ATCCATGCGA TC                                                         5859
```

(2) INFORMATION FOR SEQ ID NO:8:

(i) SEQUENCE CHARACTERISTICS:
        (A) LENGTH: 279 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gln Asn His Val Ile Ser Leu Ala Ser Ala Ala Glu Arg Arg Ala
 1               5                  10                  15

His Ile Ala Ala Thr Phe Gly Ser Arg Gly Ile Pro Phe Gln Phe Phe
            20                  25                  30

Asp Ala Leu Met Pro Ser Glu Arg Leu Glu Arg Ala Met Ala Glu Leu
        35                  40                  45

Val Pro Gly Leu Ser Ala His Pro Tyr Leu Ser Gly Val Glu Lys Ala
    50                  55                  60

Cys Phe Met Ser His Ala Val Leu Trp Glu Gln Ala Leu Asp Glu Gly
65                  70                  75                  80

Val Pro Tyr Ile Ala Val Phe Glu Asp Asp Val Leu Leu Gly Glu Gly
                85                  90                  95

Ala Glu Gln Phe Leu Ala Glu Asp Thr Trp Leu Gln Glu Arg Phe Asp
            100                 105                 110

Pro Asp Ser Ala Phe Val Val Arg Leu Glu Thr Met Phe Met His Val
        115                 120                 125

Leu Thr Ser Pro Ser Gly Val Ala Asp Tyr Gly Gly Arg Ala Phe Pro
    130                 135                 140

Leu Leu Glu Ser Glu His Cys Gly Thr Ala Gly Tyr Ile Ile Ser Arg
145                 150                 155                 160

Lys Ala Met Arg Phe Phe Leu Asp Arg Phe Ala Val Leu Pro Pro Glu
                165                 170                 175

Arg Leu His Pro Val Asp Leu Met Met Phe Gly Asn Pro Asp Asp Arg
            180                 185                 190

Glu Gly Met Pro Val Cys Gln Leu Asn Pro Ala Leu Cys Ala Gln Glu
        195                 200                 205

Leu His Tyr Ala Lys Phe His Asp Gln Asn Ser Ala Leu Gly Ser Leu
    210                 215                 220

Ile Glu His Asp Arg Arg Leu Asn Arg Lys Gln Gln Trp Arg Asp Ser
225                 230                 235                 240

Pro Ala Asn Thr Phe Lys His Arg Leu Ile Arg Ala Leu Thr Lys Ile
                245                 250                 255

Gly Arg Glu Arg Glu Lys Arg Arg Gln Arg Arg Glu Gln Leu Ile Gly
            260                 265                 270

Lys Ile Ile Val Pro Phe Gln
        275
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: PCR primer (xi) SEQUENCE DESCRIPTION: SEQ ID NO:9:

GCCGAGAAAA CTATTGGTGG A                                              21

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: PCR primer (xi) SEQUENCE DESCRIPTION: SEQ ID NO:10:

AAAACATGCA GGAATTGACG AT                                             22

(2) INFORMATION FOR SEQ ID NO:11:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:11:

Leu Gln Pro Leu Val Ser Val Leu Ile Cys Ala Tyr Asn Val Glu Lys
 1               5                  10                  15

Tyr Phe Ala Gln Ser Leu Ala Ala Val Val Asn Gln Thr Trp Arg Asn
            20                  25                  30

Leu Asp Ile Leu Ile Val Asp Asp Gly Ser Thr Asp Gly Thr Leu Ala
        35                  40                  45

Ile Ala Lys Asp Phe Gln Lys Arg Asp Ser Arg Ile Lys Ile Leu Ala
    50                  55                  60

Gln Ala Gln Asn Ser Gly Leu Ile Pro Ser Leu Asn Ile Gly Leu Asp
65                  70                  75                  80

Glu Leu Ala Lys Ser Gly Gly Gly Gly Glu Tyr Ile Ala Arg Thr
                85                  90                  95

Asp Ala Asp Asp Ile Ala Ser Pro Gly Trp Ile Glu Lys Ile Val Gly
            100                 105                 110

Glu Met Glu Lys Asp Arg Ser Ile Ile Ala Met Gly Ala Trp Leu Glu
        115                 120                 125

```
Val Leu Ser Glu Glu Lys Asp Gly Asn Arg Leu Ala Arg His His Lys
        130                 135                 140

His Gly Lys Ile Trp Lys Lys Pro Thr Arg His Glu Asp Ile Ala Ala
145                 150                 155                 160

Phe Phe Pro Phe Gly Asn Pro Ile His Asn Asn Thr Met Ile Met Arg
                165                 170                 175

Arg Ser Val Ile Asp Gly Gly Leu Arg Tyr Asp Thr Glu Arg Asp Trp
            180                 185                 190

Ala Glu Asp Tyr Gln Phe Trp Tyr Asp Val Ser Lys Leu Gly Arg Leu
        195                 200                 205

Ala Tyr Tyr Pro Glu Ala Leu Val Lys Tyr Arg Leu His Ala Asn Gln
    210                 215                 220

Val Ser Ser Lys His Ser Val Arg Gln His Glu Ile Ala Gln Gly Ile
225                 230                 235                 240

Gln Lys Thr Ala Arg Asn Asp Phe Leu Gln Ser Met Gly Phe Lys Thr
                245                 250                 255

Arg Phe Asp Ser Leu Glu Tyr Arg Gln Thr Lys Ala Ala Ala Tyr Glu
            260                 265                 270

Leu Pro Glu Lys Asp Leu Pro Glu Glu Asp Phe Glu Arg Ala Arg Arg
        275                 280                 285

Phe Leu Tyr Gln Cys Phe Lys Arg Thr Asp Thr Pro Pro Ser Gly Ala
    290                 295                 300

Trp Leu Asp Phe Ala Ala Asp Gly Arg Met Arg Arg Leu Phe Thr Leu
305                 310                 315                 320

Arg Gln Tyr Phe Gly Ile Leu Tyr Arg Leu Ile Lys Asn Arg Arg Gln
                325                 330                 335

Ala Arg Ser Asp Ser Ala Gly Lys Glu Gln Glu Ile
            340                 345

(2) INFORMATION FOR SEQ ID NO:12:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:12:

Leu Gln Pro Leu Val Ser Val Leu Ile Cys Ala Tyr Asn Ala Glu Lys
1               5                   10                  15

Tyr Phe Ala Gln Ser Leu Ala Ala Val Val Gly Gln Thr Trp Arg Asn
                20                  25                  30

Leu Asp Ile Leu Ile Val Asp Asp Gly Ser Thr Asp Gly Thr Pro Ala
            35                  40                  45

Ile Ala Arg His Phe Gln Glu Gln Asp Gly Arg Ile Arg Ile Ile Ser
    50                  55                  60

Asn Pro Arg Asn Leu Gly Phe Ile Ala Ser Leu Asn Ile Gly Leu Asp
65                  70                  75                  80

Glu Leu Ala Lys Ser Gly Gly Gly Glu Tyr Ile Ala Arg Thr Asp Ala
                85                  90                  95

Asp Asp Ile Ala Ser Pro Gly Trp Ile Glu Lys Ile Val Gly Glu Met
            100                 105                 110

Glu Lys Asp Arg Ser Ile Ile Ala Met Gly Ala Trp Leu Glu Val Leu
        115                 120                 125

Ser Glu Glu Asn Asn Lys Ser Val Leu Ala Ala Ile Ala Arg Asn Gly
```

-continued

```
              130                 135                 140
Ala Ile Trp Asp Lys Pro Thr Arg His Glu Asp Ile Val Ala Val Phe
145                 150                 155                 160

Pro Phe Gly Asn Pro Ile His Asn Asn Thr Met Ile Met Arg Arg Ser
                165                 170                 175

Val Ile Asp Gly Gly Leu Arg Phe Asp Pro Ala Tyr Ile His Ala Glu
            180                 185                 190

Asp Tyr Lys Phe Trp Tyr Glu Ala Gly Lys Leu Gly Arg Leu Ala Tyr
        195                 200                 205

Tyr Pro Glu Ala Leu Val Lys Tyr Arg Phe His Gln Asp Gln Thr Ser
    210                 215                 220

Ser Lys Tyr Asn Leu Gln Gln Arg Arg Thr Ala Trp Lys Ile Lys Glu
225                 230                 235                 240

Glu Ile Arg Ala Gly Tyr Trp Lys Ala Ala Gly Ile Ala Val Gly Ala
                245                 250                 255

Asp Cys Leu Asn Tyr Gly Leu Leu Lys Ser Thr Ala Tyr Ala Leu Tyr
            260                 265                 270

Glu Lys Ala Leu Ser Gly Gln Asp Ile Gly Cys Leu Arg Leu Phe Leu
        275                 280                 285

Tyr Glu Tyr Phe Leu Ser Leu Glu Lys Tyr Ser Leu Thr Asp Leu Leu
    290                 295                 300

Asp Phe Leu Thr Asp Arg Val Met Arg Lys Leu Phe Ala Ala Pro Gln
305                 310                 315                 320

Tyr Arg Lys Ile Leu Lys Lys Met Leu Arg Pro Trp Lys Tyr Arg Ser
                325                 330                 335

Tyr
```

GLYCOSYLTRANSFERASES FOR BIOSYNTHESIS OF OLIGOSACCHARIDES, AND GENES ENCODING THEM

This is a continuation of application Ser. No. 08/683,426, filed Jul. 18, 1996, which issued as U.S. Pat. No. 5,705,767 on Jan. 6, 1998, which is a division of application Ser. No. 08/312,387, filed Sep. 26, 1994, which issued as U.S. Pat. No. 5,545,553 on Aug. 13, 1996.

The research leading to the present invention was supported in part with funds from grant number AI-10615 from the Public Health Service. Accordingly, the Government may have certain rights in the invention.

FIELD OF THE INVENTION

The present invention relates to glycosyltransferases useful for biosynthesis of oligosaccharides, genes encoding such glycosyltransferases and recombinant methods of producing the enzymes, and the oligosaccharides produced thereby.

BACKGROUND OF THE INVENTION

Neisseria and Lipo-oligosaccharide (LOS)

While Neisseria species commonly colonize many mammalian hosts, human beings are the only species subject to invasive disease by members of this species. *Neissena meningitidis* is the etiologic agent for septicemia and meningitis that may occur in epidemic form. *Neisseria gonorrhoeae* is the causative agent of gonorrhea and its manifold complications. These organisms, particularly the gonococcus, have proved remarkably adept at varying the antigenic array of their surface-exposed molecules, notably their adhesive pili and opacity-related (opa) proteins. The genetic mechanisms for the variation of pilus (Meyer et al., 1982, Cell 30:45; Haas and Meyer, 1986, Cell 44:107; Koomey et al., 1987, Genetics 117:391; Swanson and Koomey, 1989, American Society for Microbiology, Washington, 743–761) and opa protein (Stem et al., 1986, Cell 47:61; Meyer et al., 1990, Ann. Rev. Microbiol. 44:451; Bhat et al., 1991, Molec. Microbiol. 5:1889) expression are in the main well understood. Like other Gram-negative bacteria the Neisseria ssp. carry LPS in the external leaflet of their outer membranes (Johnston and Gotschlich, 1974, J. Bacteriol. 119;250). In contrast to the high molecular weight LPS molecules with repeating O-chains seen in many enteric bacteria, the LPS of Neisseria ssp. is of modest size and therefore is often referred to as lipooligosaccharide or LOS. Although the molecular size of the LOS is similar to that seen in rough LPS mutants of Salnonella ssp., this substance has considerable antigenic diversity. In the case of the meningococcus, a serological typing scheme has been developed that separates strains into 12 immunotypes (Zollinger and Mandrell, 1977, Infect. Immun. 18:424; Zollinger and Mandreli, 1980, Infect. Immun. 28:451). A remarkably complete understanding of the structure of meningococcal LPS (recently reviewed (Verheul et al., 1993, Microbiol. Rev. 57:34) has resulted from the studies of Jennings and his colleagues (Jennings et al., 1983, Carbohyd. Res. 121:233; Michon et al., 1990, J. Biol. Chem. 265:7243; Gamian et al., 1992, J. Biol. Chem. 267:922; Pavliak et al., 1993, J. Biol. Chem. 268:14146). In the case of *Neisseria gonorrhoeae*, antigenic variability is so pronounced that a serological classification scheme has proved elusive. In part this is due to the heterogeneity of LOS synthesized by a particular strain; LOS preparations frequently contain several closely spaced bands by SDS-PAGE (Mandrell et al., 1986, Infect. Immun. 54:63). Further, studies using monoclonal antibodies indicate, that gonococci are able to change the serological characteristics of the LOS they express and that this antigenic variation occurs at a frequency of $10^{-2}$ to $10^{-3}$, indicating that some genetic mechanism must exist to achieve these high frequency variations (Schneider et al., 1988, Infect. Immun. 56:942; Apicella et al., 1987, Infect. Immun. 55:1755). Because of the molecular heterogeneity and antigenic variation of the LOS produced by gonococci the determination of the structural chemistry of this antigen has proved to be a difficult problem, and definitive information based on very sophisticated analyses has only recently become available (Yamasaki et al, 1991, Biochemistry 30:10566; Kerwood et al., 1992, Biochemistry 31:12760; John et al., 1991, J. Biol. Chem. 266:19303; Gibson et al., 1993, J. Bacteriol. 175:2702). These are summarized in FIG. 1. Of particular interest is the presence of the tetrasaccharide Gal$\beta$1→4GlcNAc$\beta$1→3Gal$\beta$1→4Glc$\beta$1→4, which is a perfect mimic of lacto-N-neotetraose of the sphingolipid paraglobosidc (Mandrell et al., 1988, J. Exp. Med. 168:107; Tsai and Civin, 1991, Infect. Immun. 59:3604). In LOS this tetrasaccharide frequently bears an additional N-acetyl galactosamine residue (GalNAc$\beta$1→3Gal$\beta$1→4GlcNAc$\beta$1→3Gal$\beta$1→4Glc$\beta$1→4), and then mimics gangliosides. In some strains of gonococci an alternative side chain is found which has the structure Gal$\alpha$1→4Gal$\beta$1→4Glc$\beta$1→4Hep→R (John et al., 1991, J. Biol. Chem. 266:19303). This is a mimic of the saccharide portion of globoglycolipids (Mandrell, 1992, Infect. Tmmun. 60:3017), and is the structure characteristically found in *Neisseria meningitides* immunotype L1.

The LOS molecules have a number of biological activities. They are potent endotoxic molecules believed to be the toxin responsible for adrenal cortical necrosis seen in severe meningococcal disease. They serve as the target a for much of the bactericidal activity present in normal or convalescent human sera (Rice et al., 1980, J. Immunol. 124:2105). Gonococci possess a very unusual sialyl transferase activity which is able to use externally supplied CMP-NANA and add N-acetyl neuraminic acid to the LOS on the surface of the organism (Nairn et al., 1988, J. Gen. Microbiol. 134:3295; Parsons et al., 1989, Microb. Pathog. 7:63; Mandrell et al., 1990, J. Exp. Med. 171:1649). Group B and C meningococci, have the capacity to synthesize CMP-NANA, and frequently sialylate their LOS without requiring exogenous CMP-NANA (Mandrell et al., 1991, J. Bacteriol. 173:2823). In *Neisseria meningitidis* strain 6275 immunotype L3, the sialic acid unit is linked $\alpha$2→3 to the terminal Gal residue of the lacto-N-neotetraose (Yamasaki et al., 1993, J. Bacteriol. 175:4565). The levels of CMP-NANA found in various host environments is sufficient to support this reaction (Apicella et al., 1990, J. Infect. Dis. 162:506). The sialylation of the LOS causes gonococci to become resistant to the antibody-complement dependent bactericidal effect of serum (Parsons et al., 1989, Microb. Pathog. 7:63). The resistance is not only to the bactericidal effect mediated by antibodies to LOS, but to other surface antigens as well (Wetzler et al., 1992, Infect. Immun. 60:39). van Putten has demonstrated that exposure of gonococci to CMP-NANA markedly reduces their ability to invade epithelial cells in tissue culture (Van Putten, 1993, EMBO J. 12:4043). These findings strongly suggest that the ability of gonococci to vary the chemical nature of the LOS provides them with the ability to cope with different host environments (Mandrell and Apicella, 1993, Immunobiology 187:382).

Perhaps most telling, it has been found that LOS variation is selected in vivo in infections of human beings. A well characterized gonococcal laboratory strain MS11$_{mk}$ variant A was used to inoculate volunteers (Swanson et al., 1988, J. Exp. Med. 168:2121). In the two infected individuals over a period of 4 to 6 days the population of gonococci recovered in their urine increasingly shifted to two variants that expressed antigenically different LOS (Schneider et al., 1991, J. Exp. Med. 174:1601). A structural analysis revealed that the inoculated variant A produced a truncated LOS containing only the β-lactosyl group linked to Hep1, while one of the new variants (variant C) produced a complete LOS (Kerwood et al., 1992, Biochemistry 31:12760). This suggests that the addition of the additional sugars GalNAcβ1→3Galβ1→4GlcNAcβ1→3 is likely to be under control of a phase variation mechanism.

Little information on the genetics of LOS synthesis of in Neisseria is available. A major advance has been the creation (Dudas and Apicella, 1988, Infect. Immun. 56:499) and biochemical characterization (John et al., 1991, J. Biol. Chem. 266:19303) of five pyocin mutants of gonococcal strain 1291, dubbed 1291a–e. Immunological and biochemical data have shown that 1291a, 1291c, 1291d and 1291e produce LOS with sequential shortening of the lacto-N-neotetraose chain, with mutant 1291e lacking the glucose substitution on the heptose. Mutant 1291b synthesizes the alternative LOS structure Galα1→4Galβ1→4Glc (see FIG. 1). Only the genetic basis of the 1291e mutant is now defined. It is a mutation of phosphoglucomutase (pgm), which precludes the synthesis of UDP-glucose, and hence the addition of the first residue of the lacto-N-neotetraose unit (Zhou et al., 1994, J. Biol. Chem. 269:11162; Sandlin and Stein, 1994, J. Bacteriol. 176:2930). It also has been shown that galE mutants of meningococcus or gonococcus produce truncated LOS in keeping with the inability to synthesize UDP-galactose (Robertson et al., 1993, Molec. Microbiol. 8:891; Jennings et al., 1993, Molec. Microbiol. 10:361).

Biosynthesis of Oligosaccharides

Oligosaccharides are polymers of varying number of residues, linkages, and subunits. The basic subunit is a carbohydrate monosaccharide or sugar, such as mannose, glucose, galactose, N-acetylglucosamine, N-acetylgalactosamine, and the like. The number of different possible stereoisomeric oligosaccharide chains is enormous.

Oligosaccharides and polysaccharides play an important role in protein function and activity, by serving as half-life modulators, and, in some instances, by providing structure. As pointed out above, oligosaccharides are critical to the antigenic variability, and hence immune evasion, of Neisseria, especially gonococcus.

Numerous classical techniques for the synthesis of carbohydrates have been developed, but these techniques suffer the difficulty of requiring selective protection and deprotection. Organic synthesis of oligosaccharides is further hampered by the lability of may glycosidic bonds, difficulties in achieving regio-selective sugar coupling, and generally low synthetic yields. In short, unlike the experience with peptide synthesis, traditional synthetic organic chemistry cannot provide for quantitative, reliable synthesis of even fairly simple oligosaccharides.

Recent advances in oligosaccharide synthesis have occurred with the isolation of glycosyltransferases. These enzymes can be used in vitro to prepare oligosaccharides and polysaccharides (see, e.g., Roth, U.S. Pat. No. 5,180,674, issued Jan. 19, 1993). The advantage of biosynthesis with glycosyltransferases is that the glycosidic linkages formed by enzymes are highly stereo and regio-specific. However, each enzyme catalyzes linkage of specific sugar residues to other specific acceptor molecules, e.g., an oligosaccharide or lipid. Thus, synthesis of a desired oligosaccharide may be limited by the availability of glycosyltransferases (see, Roth, International Patent Publication No. WO 93/13198, published Jul. 8, 1993).

Another drawback of biosynthesis is that the glycosyltransferases themselves are usually present in fairly low quantities in cells. It is difficult to obtain enough of the enzyme to be commercially practicable.

Thus, there is a great need in the art for glycosyltransferases. There is a further need for genes encoding such glycosyltransferases, to provide an unlimited source of glycosyltransferases through recombinant technology.

The citation of any reference herein should not be construed as an admission that such reference is available as prior art to the instant invention.

SUMMARY OF THE INVENTION

The present invention is directed to nucleic acids encoding glycosyltransferases, the proteins encoded thereby, and to methods for synthesizing oligosaccharides using the glycosyltransferases of the invention. Accordingly, in one aspect, the invention is directed to a purified nucleic acid that is hybridizable under moderately stringent conditions to a nucleic acid corresponding to the LOS locus of Neisseria, e.g., a nucleic acid having a nucleotide sequence corresponding to or complenentary to the nucleotide sequence shown in (SEQ ID NO:1). Preferably, the nucleic acid of the invention is hybridizable to a portion of the coding sequence for a gene of the LOS locus, i.e., a portion of the nucleotide sequence shown in (SEQ ID NO:1) that encodes a functionally-active glycosyltransferase.

In specific embodiments, the invention relates to a nucleic acid that has a nucleotide sequence corresponding to or complementary to a portion of the nucleotide sequence shown in (SEQ ID NO:1) that encodes a functionally active glycosyltransferase. In a further aspect, the nucleic acid encodes a functionally active glycosyltransferase. In a specific embodiment, the invention is directed to a nucleic acid that has a nucleotide sequence corresponding to or complementary to the nucleotide sequence shown in (SEQ ID NO:1).

The functionally active glycosyltransferases of the invention are characterized by catalyzing a reaction selected from the group consisting of:

adding Gal β1→4 to GlcNAc or Glc;
adding GalNAc or GlcNAc β1→3 to Gal; and
adding Gal α1→4 to Gal.

Most preferably, the claimed nucleic acid encodes a functionally active glycosyltransferase. However, nucleic acids of the invention include oligonucleotides useful as primers for polymerase chain reaction (PCR) or for probes for the presence and level of transcription of a glycosyltransferase gene.

In specific embodiments, exemplified herein, the nucleic acid encodes a glycosyltransferase having an amino acid sequence of; SEQ ID NO:3 or SEQ ID NO:11, SEQ ID NO:4, SEQ ID NO:5 or SEQ ID NO:12, or SEQ ID NO:6, or SEQ ID NO:8.

The invention further relates to an expression vector comprising the nucleic acid encoding a glycosyltransferase of the invention operatively associated with an expression control sequence. Accordingly, the invention extends to recombinant host cell transformed with such an expression vector.

In another aspect, the invention is directed to a method for producing a glycosyltransferase comprising culturing the recombinant host cell under conditions that allow expression of the glycosyltransferase; and recovering the expressed glycosyltransferase.

In a primary aspect, the invention is directed to glycosyltransferase having an amino acid sequence of, SEQ ID NO:3 or SEQ ID NO:11, SEQ ID NO:4, SEQ ID NO:5 or SEQ ID NO:12, SEQ ID NO:6, or SEQ ID NO:8, or a functionally active fragment thereof. The invention further contemplates a composition comprising a glycosyltransferase conjugated to a solid phase support, wherein the glycosyltransferase is selected from the group consisting of a glycosyltransferase having an amino acid sequence of SEQ ID NO:3, or SEQ ID NO:11 or a functionally active fragment thereof; a glycosyltransferase having an amino acid sequence of SEQ ID NO:8, or a functionally active fragment thereof; a glycosyltransferase having an amino acid sequence of SEQ ID NO:4, or a functionally active fragment thereof; and a glycosyltransferase having an amino acid sequence of SEQ ID NO:5 or SEQ ID NO:12, or a functionally active fragment thereof; and a glycosyltransferase having an amino acid sequence of SEQ ID NO:6, or a functionally active fragment thereof.

Having provided novel glycosyltransferases, and genes encoding the same, the invention accordingly further provides methods for preparing oligosaccharides, e.g., two or more saccharides. In specific embodiments, the invention relates to a method for adding GalNAc or GlcNAc β1→3 to Gal, comprising contacting a reaction mixture comprising an activated GalNAc or GlcNAc to an acceptor moiety comprising a Gal residue in the presence of the glycosyltransferase having an amino acid sequence of SEQ ID NO:3 or SEQ ID NO:11; a method for adding Gal β1→4 to GlcNAc or Glc, comprising contacting a reaction mixture comprising an activated Gal to an acceptor moiety comprising a GlcNAc or Glc residue in the presence of the glycosyltransferase having an amino acid sequence of SEQ ID NO:8; a method for adding Gal α1→4 to Gal, comprising contacting a reaction mixture comprising an activated Gal to an acceptor moiety comprising a Gal residue in the presence of the glycosyltransferase having an amino acid sequence of SEQ ID NO:4; a method for adding GalNAc or GlcNAc β1→3 to Gal, comprising contacting a reaction mixture comprising an activated GalNAc or GlcNAc to an acceptor moiety comprising a Gal residue in the presence of the glycosyltransferase having an amino acid sequence of SEQ ID NO:5 SEQ ID NO:12; and a method for adding Gal β1→4 to GlcNAc or Glc, comprising contacting a reaction mixture comprising an activated Gal to an acceptor moiety comprising a GlcNAc or Glc residue in the presence of the glycosyltransferase having an amino acid sequence of SEQ ID NO:6.

In a preferred embodiment, the oligosaccharides are prepared on a carrier that is non-toxic to a mammal, in particular a human, such as a lipid isoprenoid or polyisoprenoid alcohol. A specific example of such a carrier is dolichol phosphate. In a specific embodiment, the oligosaccharide is attached to the carrier via a labile bond, thus allowing for chemically removing the oligosaccharide from the lipid carrier. Alternatively, an oligosaccharide transferase can be used, e.g., to transfer the oligosaccharide from a lipid carrier to a protein. In yet another embodiment, the glycosyltransferases can be expressed in a eukaryotic expression system, to provide for glycosylation of a protein expressed in such a system.

An important advantage of the present invention is that it provides for the synthesis of oligosaccharide antigens of Neisseria independently of lipid A, which is highly toxic. Use of the natural LOS from Neisseria, while theoretically desirable for vaccine preparation, fails. The lipid A portion of LOS is a potent endotoxin, and highly toxic. Chemical treatment of the LOS, e.g., by hydrolysis, destroys the antigenicity of the oligosaccharide, leaving a useless product. Thus, it is highly desirable to have a source of Neisseria oligosaccharides attached to non-toxic lipids for vaccine preparation.

Thus, the invention provides glycosyltransferases and strategies for preparing a number of oligosaccharides, such as but not limited to, Galα1→4Galβ1→4Glc, Galβ1→4GlcNAcβ1→3Galβ1→4Glc, and GalNAcβ1→3Galβ1→4GlcNAcβ1→3Galβ1→4Glc.

Accordingly, it is a primary object of the invention to provide glycosyltransferases useful for the synthesis of oligosaccharides.

It is a further object of the invention to provide for the synthesis of oligosaccharides characteristic of *Neisseria meningitidis* and *N. gonorrhoeae*.

It is a further object of the invention to provide for the synthesis of oligosaccharides characteristic of mammalian oligosaccharides, including blood group core oligosaccharides.

It is still a further object of the invention to provide for vaccines having the oligosaccharide unit of LOS, but lacking lipid A.

Still a further object of the invention is to provide for synthesis of therapeutically useful oligosaccharides.

These and other objects of the present will be made clear by reference to the following Drawings and Detailed Description.

BRIEF DESCRIPTION OF THE DRAWINGS

FIG. 1: Alternative structures found in gonococcal LOS. R1 refers to the inner core region of LOS consisting of two keto-deoxy-octulosonic acid (KDO) residues. These in turn are attached to a lipid A structure. R2 in gonococci is typically GlcNAcβ1→2Hepα1→3. The structure in the top panel contains a tetrasaccharide identical to lacto-N-neotetraose found in paragloboside glycolipids. In many strains this tetrasaccharide bears a terminal GalNAcβ1→3. The lower panel shows an alternative trisaccharide structure with the terminal Gal α1→4 linked. This trisaccharide is seen in meningococci of the L1 serotype and in some gonococcal strains. The portions of the two structures recognized by the monoclonal antibodies used in this study are indicated (4C4) (Dudas and Apicella, 1988, Infect. Immun. 56:499) 3F11 (Mandrell et al., 1988, J. Exp. Med. 168–107; Yamasaki et al., 1991, Mol. Immunol. 28:1233) 1-1-M (Yamasaki et al., 1991, Mol. Immunol. 28:1233), 2-1-L8 (Kerwood et al., 1992, Biochemistry 31:12760; Schneider et al., 1991, J. Exp. Med. 174:1601; Schneider et al., 1985, Infect. Immun. 50:672) 9-2-L378 and 17-1-L1.

FIGS. 3(A and B): Homology of the protein products of lgtA (SEQ ID NO:11) and lgtD (SEQ ID NO:12). The primary structure of two proteins is very similar, particularly in the first half of the sequences. The glycine residues starting at position 86 reflect the coding of the poly-G regions in the respective genes. The Bestfit program of the GCG package was used and the symbols |, :, . represent degrees of similarity based on the Dayhoff PAM-250 matrix.

FIGS. 4(A and B): Homology of the protein products of lgtB and lgtE. The primary structure of two proteins is very similar, particularly in the first half of the sequences. These sequences also have significant homology to lex-1 (Cope et al., 1991, Molec. Microbiol. 5:1113) or lic2A (High et al., 1993, Molec. Microbiol. 9:1275) genes of *Haemophilus influenzae*. For meaning of symbols see FIG. 3.

FIG. 5(A and B): Homology of the protein products of rfaI and lgtC. The *E. coli* rfaI and rfaJ genes are very closely related. They serve as glucosyl transferases of two glucose residues in the LPS core region (Pradel et al., 1992, J. Bacteriol. 174:4736). The glycines at position 54–56 in lgtC are encoded by the poly-G tract. For meaning of symbols see FIG. 3.

DETAILED DESCRIPTION OF THE INVENTION

Figure 2A:
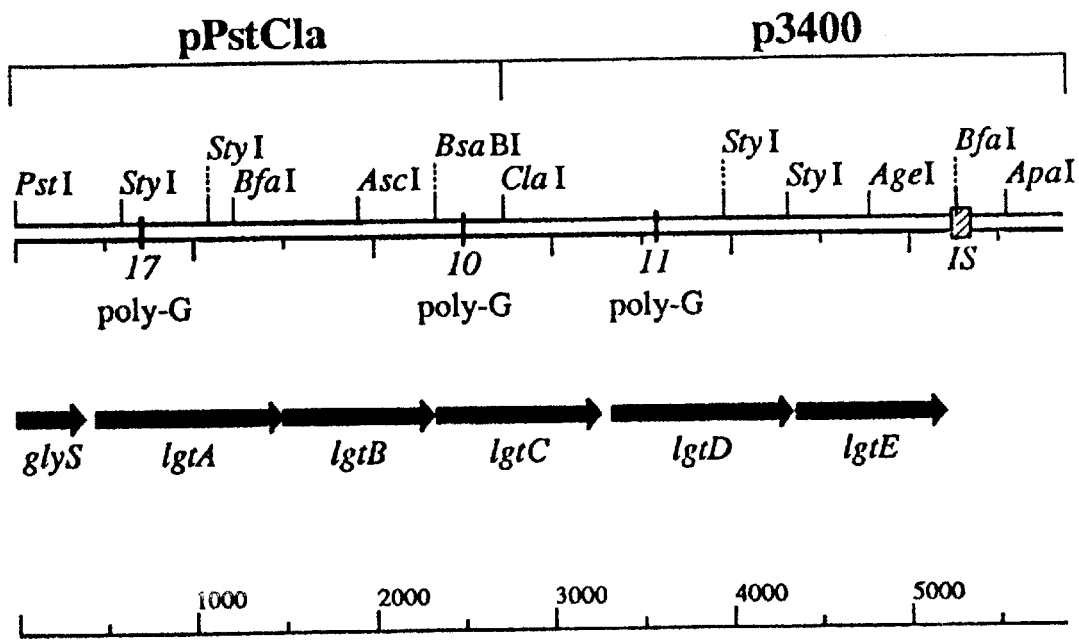
FIG. 2: Genetic map of the LOS locus based on the DNA sequence. Sequence information bp 1-2725 was obtained from plasmid pPstCla, bp 2725–5859 from plasmid p3400 (see materials and methods). IS refers to an area of the sequence that has homology to a previously reported neisserial insertion see IS1106 (Knight et al., 1992, Molec. Microbiol. 6:1565). The positions of the reading frames of lgtA-E are indicated. Three tracts of poly-G were found in lgtA (17 bp), lgtC (10 bp) and lgtd (11 bp) and are indicated by vertical black bars.

As disclosed above, the present invention provides five novel glycosyltransferases, genes encoding the glycosyltransferases, and methods for biosynthesis of oligosaccharides using such glycosyltransferases. The glycosyl transferases of the invention can be used for in vitro biosynthesis of various oligosaccharides, such as the core oligosaccharide of the human blood group antigens, i.e., lacto-N-neotetraose.

Cloning and expression of glycosyltransferases of the invention can be accomplished using standard techniques, as disclosed herein. Such glycosyl transferases are useful for biosynthesis of oligosaccharides in vitro, or alternatively genes encoding such glycosyltransferases can be transfected into cells, e.g., yeast cells or eukaryotic cells, to provide for alternative glycosylation of proteins and lipids.

The instant invention is based, in part, on the discovery and cloning of a locus involved in the biosynthesis of gonococcal LOS has from gonococcal strain F62. The locus contains five open reading frames. The first and the second reading frames are homologous, but not identical to the fourth and the fifth reading frames respectively. Interposed is an additional reading frame which has distant homology to the *E. coli* rfaI and rfaJ genes, both glucosyl transferases involved in LPS core biosynthesis. The second and the fifth reading frames show strong homology to the lex-1 or lic2A gene of *Haemophilus influenzae*, but do not contain the CAAT repeats found in this gene. Deletions of each of these five genes, of combinations of genes, and of the entire locus were constructed and introduced into parental gonococcal strain F62 by transformation. The LOS phenotypes were then analyzed by SDS-PAGE and reactivity with monoclonal antibodies. Analysis of the gonococcal mutants indicates that four of these genes are the glycosyl transferases that add GalNAcβ1→3Galβ1→4GlcNAcβ1→3Galβ1→4 to the substrate Glcβ1→4Hep→R of the inner core region. The gene with homology to *E. coli* rfaI/rfaJ is involved with the addition of the α-linked galactose residue in the biosynthesis of the alternative LOS structure Galα1→4Galβ1→4Glcβ1→4Hep→R.

Since these genes encode LOS glycosyl transferases they have been named lgta, lgtB, lgtC, lgtD and lgtE. The DNA sequence analysis revealed that lgtA, lgtC and lgtD contain poly-G tracts, which in strain F62 were respectively 17, 10 and 11 bp. Thus, three of the LOS biosynthetic enzymes are potentially susceptible to premature termination by reading-frame changes. It is likely that these structural features are responsible for the high frequency genetic variation of gonococcal LOS.

Abbreviations used throughout this specification include: Lipopolysaccharide, LPS; Lipooligosaccharide, LOS; N-Acetyl-neuraminic acid cytidine mono phosphate, CMP-NANA; wild type, wt; Gal, galactose; Glc, glucose; NAc, N-acetyl (e.g., GalNAc or GlcNAc).

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B .D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A cell has been "transformed" by exogenous or heterologous DNA when such DNA has been introduced inside the cell; the cell may express a gene or genes encoded by such DNA. The transforming DNA may or may not be integrated (covalently linked) into chromosomal DNA making up the genome of the cell, or may be contained on an autonomous replicon. In prokaryotes, yeast, and mammalian cells for example, the transforming DNA may be maintained on an episomal element such as a plasmid. A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA hebices are possible. The term nucleic acid molecule, and in particular DNA or RNA molecule, refers only to the primary and secondary structure of the molecule, and does not limit it to any particular tertiary forms. Thus, this term includes doublestranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementary, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

A DNA "coding sequence" is a double-stranded DNA sequence which is transribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. Although the individual genes encoding glycosyltransferases of the invention are found in a single locus with very short non-coding sequences between them, phase variation resulting in deletion of any of lgtA, lgtB, or lgtC does not preclude reinitiation of transcription at the downstream genes. Thus, the locus provided herein includes trascription initiation sequences for transcription in Neisseria. Alternatively, the coding sequences of the invention can be engineered for expression under control of heterologous control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above backgroud. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that directs the host cell to translocate the polypeptide to the cell surface or to organelles within the cell, or secrete the polypeptide into the media, and this signal peptide is usually selectively cleaved by the protein transport machinery. Signal sequences can be found associated with a variety of proteins native to prokaryotes and eukaryotes. Incorporation of a signal sequence may be desirable for high level expression of a glycosyltransferase of the invention by bacteria, yeast, insect cells (baculovirus), or eukaryotic cells, to avoid affecting endogenous glycosyltransfer in the host cell.

A molecule is "antigenic" when it is capable of specifically interacting with an antigen recognition molecule of the immune system, such as an immunoglobulin (antibody) or T cell antigen receptor. As mentioned above, the carbohydrate (oligosaccharide) moiety of the LOS of Neisseria is an important antigenic determinant, which determines serotype of meningococcus (Zollinger and Mandrell, 1977, Infect. Immun. 18:424; Zollinger and Mandrell, 1980, Infect. Immun. 28:451). An antigenic portion of a molecule can be that portion that is immunodominant for antibody, or it can be a portion used to generate an antibody to the molecule by conjugating the antigenic portion to a carrier molecule for inmmunization. A molecule that is antigenic need not be itself immunogenic, i.e., capable of eliciting an immune response without a carrier.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil an the like. Water or aqueous solution saline solutions and aqueous dextrose and glycerol solutions are preferably employed as carriers, particularly for injectable solutions. Pharmaceutically acceptable compositions of the invention are free of amounts of lipid A effective to cause a response in a mammalian subject, in particular a human subject.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Preferably, the adjuvant is pharmaceutically acceptable.

Isolation of Genes for Glycosyltransferases

The present invention provides the full length coding sequence of the LOS locus of Neisseria, and thus, allows for obtaining any one or all five genes, termed herein lgt genes, encoding glycosyltransferases characteristic of that locus. Any Neisseria bacterial cell can potentially serve as the nucleic acid source for the molecular cloning of an lgt gene. In a specific embodiment, infra, the genes are isolated from *Neisseria gonorrhoeae*. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). For example, a *N. gonorrhoeae* genomic DNA can be digested with a restriction endonuclease or endonucleases, e.g., Sau3A, into a phage vector digested with a restriction endonuclease or endonucleases, e.g., BamHI/EcoRI, for creation of a phage genomic library. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired lgt gene may be accomplished in a number of ways. For example, the generated DNA fragments may be screened by nucleic acid hybridization to the labeled probe synthesized with a sequence as disclosed herein (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for glycosyltransferases, e.g., SEQ ID NO:1.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, or functional properties, in particular glycosyltransferase activity the ability of a Lgt protein to mediate transfer of a sugar to an acceptor molecule. Alternatively, the putative lgt gene can be mutated, and its role as a glycosyltransferase established by detecting a variation in the structure of the oligosaccharide of LOS.

Alternatives to isolating the lgt genomic DNA include, but are not limited to, chemically synthesizing the gene sequence itself from a known sequence that encodes an Lgt, e.g., as shown in SEQ ID NO:1. In another embodiment, DNA for an lgt gene can be isolated PCR using oligonucleotide primers designed from the nucleotide sequences disclosed herein. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. In a specific aspect of the invention, the lgt coding sequence is inserted in an *E. coli* cloning vector. Other examples of vectors include, but are not limited to, bacteriophages such as lambda derivatives, or plasmids such as pBR322 derivatives or pUC plasmid derivatives, e.g., PGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In specific embodiment, PCR primers containing such linker sites can be used to amplify the DNA for cloning. Recombinant molecules can be introduced into host cells via transformation, transfection, infection, electroporation, etc., so that many copies of the gene sequence are generated.

Transformation of host cells with recombinant DNA molecules that incorporate the isolated lgt gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding truncated forms of the enzyme (fragments) and derivatives of Lgt's that have the same functional activity as an Lgt. The production and use of fragments and derivatives related to an Lgt are within the scope of the present invention. In a specific embodiment, the fragment or derivative is functionally active, i.e., capable of mediating transfer of a sugar to an acceptor molecule.

Truncated fragments of the glycosyltransferases can be prepared by eliminating N-terminal, C-terminal, or internal regions of the protein that are not required for functional activity. Usually, such portions that are eliminated will include only a few, e.g., between 1 and 5, amino acid residues, but larger segments may be removed.

Chimeric molecules. e.g., fusion proteins, containing all or a functionally active portion of a glycosyltransferase of the invention joined to another protein are also envisioned. A glycosyltransferase fusion protein comprises at least a functionally active portion of a non-glycosyltransferase protein joined via a peptide bond to at least a functionally active portion of a glycosyltransferase polypeptide. The non-glycosyltransferase sequences can be amino- or carboxy-terminal to the glycosyltransferase sequences. Expression of a fusion protein can result in an enzymatically inactive glycosyltransferase fusion protein. A recombinant DNA molecule encoding such a fusion protein comprises a sequence encoding at least a functionally active portion of a non-glycosyltransferase protein joined in-frame to the glycosyltransferase coding sequence, and preferably encodes a cleavage site for a specific protease, e.g., thrombin or Factor Xa, preferably at the glycosyltransferase-non-glycosyltransferase juncture. In a specific embodiment, the fusion protein may be expressed in *Escherichia coli.*

In particular, Lgt derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an lgt gene may be used in the practice of the present invention. These include but are not limited to nucleotide sequences comprising all or portions of lgt genes that are altered by the substitution of different codons that encode the same amino acid residue within the sequence, thus producing a silent change. Likewise, the Lgt derivatives of the invention include, but are not limited to, those containing, as a primary amino acid sequence, all or part of the amino acid sequence of an Lgt including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding Lgt derivatives and analogs of the invention can be produced by various methods known in the art (e.g., Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of Lgt, care should be taken to ensure that the modified gene remains within the same translational reading frame as the lgt gene, uninterrupted by translational stop signals, in the gene region where the desired activity is encoded.

Additionally, the lgt nucleic acid sequence can be mutated in vitro or in vivo, to create and/or destroy translation, initiating, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70). It is notable in this regard that the lgtA lgtB, and lgtC genes contain long poly-G stretches that are particularly susceptible to phase variation mutation.

Expression of a Glycosyltransferase

The gene coding for an Lgt, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native lgt gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Preferably, the periplasmic form of the Lgt (containing a signal sequence) is produced for export of the protein to the *Escherichia coli* periplasm or in an expression system based on *Bacillus subtillis.*

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an glycosyltransferase or peptide fragment may be regulated by a second nucleic acid sequence so that the glycosyltransferase or peptide is expressed in a host transformed with the recombinant DNA molecule. For example, expression of an glycosyltransferase may be controlled by any promoter/enhancer element known in the art, but these regulatory elements must be functional in the host selected for expression. For expression in bacteria, bacterial promoters are required. Eukaryotic viral or eukaryotic promoters, including tissue specific promoters, are preferred when a vector containing an lgt gene is injected directly into a subject for transient expression, resulting in heterologous protection against bacterial infection, as described in detail below. Promoters which may be used to control lgt gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; and the like Expression vectors containing lgt gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted lgt gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the lgt gene is inserted within the marker gene sequence of the vector, recombinants containing the lgt insert can be identified by the absence of the marker gene function. In the fourth approach, recombinant expression vectors can be identified by assaying for the activity of the lgt gene product expressed by the recombinant. Such assays can be based, for example, on the physical or functional properties of the lgt gene product in in vitro assay systems, e.g., glycosyltransferase activity. Once a suitable host system and growth conditions are established, recombinant expression vectors can be propagated and prepared in quantity.

Biosynthesis of Oligosaccharides

The glycosyltransferases of the present invention can be used in the biosynthesis of oligosaccharides. The glycosyltransferases of the invention are capable of stereospecific conjugation of a specific activated saccharide unit to a specific acceptor molecule. Such activated saccharides generally consist of uridine, guanosine, and cytidine diphosphate derivatives of the saccharides, in which the nucleoside diphosphate serves as a leaving group. Thus, the activated saccharide may be a saccharide-UDP, a saccharide-GDP, or a saccharide-CDP. In specific embodiments, the activated saccharide is UDP-GlcNAC, UDP-GalNAc, or UDP-Gal.

The term "acceptor molecule" as used herein refers to the molecule to which the glycosyltransferase transfers an activated sugar. As is well known in the art, synthesis of carbohydrates proceeds by sequential coupling of sugar residues to a lipid, e.g., dolichol phosphate. In eukaryotic cells, which glycosylate proteins, the oligosaccharide or polysaccharide is transferred from the activated lipid carrier to the polypeptide on the luminal side of the endoplasmic reticulum. In prokaryotes, the carbohydrate can be synthesized directly on a lipid A molecule. It is likely that the glycosyltransferases of the invention may be sensitive to the core portion of the growing carbohydrate and the lipid molecule. Thus, in a preferred aspect, the acceptor molecule, or carrier, contains a lipid, preferably a polyisoprenoid alcohol lipid such as dolichol phosphate. Maximum synthetic efficiency may ensue from use of lipid A as the carrier. While the lipid A is not useful as a carrier for direct administration of the resulting oligosaccharide to a subject, e.g., as a vaccine preparation, it may be appropriate for use with a labile linkage for subsequent cleavage (under mild conditions) and separation of the oligosaccharide from the lipid carrier. It should further be noted that the glycosyltransferases will only work efficiently to add a specific activated saccharide to a saccharide residue on the acceptor molecule that corresponds to the natural acceptor molecule. For example, LgtE catalyzes transfer of Gal to Glcβ1→4Hep. Thus, where a glycosyltransferase mediates attachment of GalNAc to Glc, the nature of the Glc residue (whether it is attached directly or indirectly to the carrier, for example) will affect the reaction efficiency. It is unlikely that efficient synthesis can occur in the absence of a carrier, or using other than a lipid carrier. However, even inefficient synthesis may be desirable, and practice of the present invention is not limited to use of acceptor molecules containing lipids, but extends to saccharides, polysaccharides, polypeptides, glycoproteins, and the like.

For the synthesis of an oligosaccharide, a glycosyltransferase is contacted with an appropriate activated saccharide and an appropriate acceptor molecule under conditions effective to transfer and covalently bond the saccharide to the acceptor molecule. Conditions of time, temperature, and pH appropriate and optimal for a particular saccharide unit transfer can be determined through routine testing; generally, physiological conditions will be acceptable. Certain co-reagents may also be desirable; for example, it may be more effective to contact the glycosyltransferase with the activated saccharide and the acceptor molecule in the presence of a divalent cation.

According to the invention, the glycosyltransferase enzymes can be covalently or non-covalently immobilized on a solid phase support such as SEPHADEX, SEPHAROSE, or poly(acrylamide-co-N-acryloxysucciimide) (PAN) resin. A specific reaction can be performed in an isolated reaction solution, with facile separation of the solid phase enzyme from the reaction products. Immobilization of the enzyme also allows for a continuous biosynthetic stream, with the specific glycosyltransferases attached to a solid support, with the supports arranged randomly or in distinct zones in the specified order in a column, with passage of the reaction solution through the column and elution of the desired oligosaccharide at the end. An efficient method for attaching the glycosyltransferase to a solid support and using such immobilized glycosyltransferases is described in U.S. Pat. No. 5,180,674, issued Jan. 19, 1993 to Roth, which is specifically incorporated herein by reference in its entirety.

An oligosaccharide, e.g., a disaccharide, prepared using a glycosyltransferase of the present invention can serve as an acceptor molecule for further synthesis, either using other glycosyltransferases of the invention, or glycosyltransferases known in the art (see, e.g., Roth, U.S. Pat. No. 5,180,674, and Roth, International Patent Publication No. WO 93/13198, published Jul. 8, 1993, each of which is incorporated herein by reference in its entirety). The oligosaccharidecompositions of the invention are useful in a wide variety of therapeutic and diagnostic applications. For example, the saccharide compositions can be used as blocking agents for cell surface receptors in the treatment of numerous diseases involving cellular adhesion. Alternatively, saccharide compositions useful as nutritional supplements, antibacterials, anti-metastases agents, anti-inflammatory agents (e.g., for binding to inflammatory-associated lectins or cell surface receptors), to mention but a few, are contemplated by the instant invention. As noted above, the glycosyltransferases of the invention can be used in conjunction with other glycosyltransferases known in the art or to be discovered to synthesize complex oligosaccharides or polysaccharides.

Alternatively, the glycosyltransferases of the invention can be used to synthesize oligosaccharides representative of the oligosaccharides found on various strains of Neisseria. For example, by deleting open reading frames from the locus, or by selecting only a few of the glycosyltransferases of the invention for synthesis, alternative oligosaccharide structures can be prepared. These can be used in vaccine preparations effective against Neisseria variants, in particular, subunit vaccines against gonococcus and meningococcus.

Alternatively, the glycosyltransferases of the present invention can be used to prepare oligosaccharides corresponding to oligosaccharides associated with human glycolipids. Thus, in specific embodiments, the present invention provides for synthesis of an oligosaccharide corresponding to lacto-N-neotetraose of the sphingolipid paragloboside; an oligosaccharide that mimics gangliosides; and a mimic of the saccharide portion of globoglycolipids, which is the structure characteristically found in *Neisseria meningitidis* immunotype L1. The oligosaccharides of the present invention correspond to the core oligosaccharides of the blood group antigens, and therefore have great utility in the preparation of such blood group antigens for diagnostic or therapeutic purposes.

Accordingly, a method for preparing an oligosaccharide having the structure GalNAcβ1→3Galβ1→4GlcNAcβ1→3Galβ1→4Glc (i.e., ganglioside) comprises sequentially performing the steps of:

a. contacting a reaction mixture comprising an activated Gal to an acceptor moiety comprising a Glc residue in the presence of a glycosyltransferase having an amino acid sequence of SEQ ID NO: 6, or a functionally active fragment thereof;

b. contacting a reaction mixture comprising an activated GlcNAc to the acceptor moiety comprising a Galβ1→4Glc residue in the presence of a glycosyltransferase having an amino acid sequence of SEQ ID NO:3 or SEQ ID NO:11, or a functionally active fragment thereof;

c. contacting a reaction mixture comprising an activated Gal to the acceptor moiety comprising a GlcNAcβ1→3Galβ1→4Glc residue in the presence of a glycosyltransferase having an amino acid of SEQ ID NO:8; and d. contacting a reaction mixture comprising an activated GalNAc to the acceptor moiety comprising a Galβ1→4GlcNAcβ1→3Galβ1→4Glc residue in the presence of a glycosyltransferase having an amino acid sequence of SEQ ID NO:5 or SEQ ID NO:12, or a functionally active fragment thereof.

Similarly, a method for preparing an oligosaccharide having the structure Galβ1→4GlcNAcβ1→3Galβ1→4Glc (i.e., lacto-N-neotetraose) comprises sequentially performing the steps of:

a. contacting a reaction mixture comprising an activated Gal to an acceptor moiety comprising a Glc residue in the presence of a glycosyltransferase having an amino acid sequence of SEQ ID NO: 6, or a functionally active fragment thereof;

b. contacting a reaction mixture comprising an activated GlcNAc to the acceptor moiety comprising a Galβ1→4Glc residue in the presence of a glycosyltransferase having an amino acid sequence of SEQ ID NO:3 or SEQ ID NO:11, or a functionally active fragment thereof; and c. contacting a reaction mixture comprising an activated Gal to the acceptor moiety comprising a GlcNAcβ1→3Galβ1→4Glc residue in the presence of a glycosyltransferase having an amino acid of SEQ ID NO:8.

In another embodiment, a method for preparing an oligosaccharide having the structure Galα1→4Galβ1→4Glc (i.e., globoglycolipids) comprises sequentially performing the steps of:

a. contacting a reaction mixture comprising an activated Gal to an acceptor moiety comprising a Glc residue in the presence of a glycosyltransferase having an amino acid sequence of SEQ ID NO:6, or a functionally active fragment thereof; and b. contacting a reaction mixture comprising an activated Gal to the acceptor moiety comprising Galβ1→4Glc in the presence of a glycosyltransferase having an amino acid sequence of SEQ ID NO:4, or a functionally active fragment thereof.

Such oligosaccharides can be prepared using lipid A as a carrier. Preferably, if the resulting glycolipid is to be used in a vaccine, a non-toxic lipid, such as dolichol phosphate, is used as the carrier.

Vaccination

Active immunity against Neisseria strains can be induced by immunization (vaccination) with an immunogenic amount of an oligosaccharide prepared according to the present invention in admixture with an adjuvant, wherein the oligosaccharide is the antigenic component of the vaccine. Preferably, the oligosaccharide is conjugated to a carrier protein. Alternatively, where the antigen is a glycolipid, it can be incorporated in a liposome.

The oligosaccharide alone cannot cause bacterial infection, although the oligosaccharide on lipid A is toxic, and the active immunity elicited by vaccination according to the present invention can result in immediate immune response.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

A vaccine of the invention, i.e., a vaccine comprising an oligosaccharide corresponding to an antigenic determinant on a strain of Neisseria, can be administered via any parenteral route, including but not limited to intramuscular, intraperitoneal, intravenous, and the like.

Administration of an amount of a Neisseria oligosaccharide sufficient to inhibit adhesion of the bacterium to its target cell may also be effective for treating meningococcal or gonococcal infection. The required amount can be determined by one of ordinary skill using standard techniques.

Expression of Glycosyltransferases in for Intracellular Glycosylation

The present invention further contemplates transforming a host cell with a glycosyltransferase or glycosyltransferases of the invention. It is expected that expression of the glycosyltransferase, possibly in a cell lacking one or more endogenous glycosyltransferases, may result in novel glycosylation of lipids and proteins in such eukaryotic cells, and novel glycosylation of lipids in procaryotic cells.

For example, transformation of a bacterium with nontoxic lipid molecules may provide for expression of Neisseria oligosaccharides on such a bacterium, which can then be used directly in a whole cell vaccine.

Alternatively, expression of such a glycosyl transferase in yeast, insect, or mammalian cell lines may result in novel glycosylation of lipids and proteins expressed by these cells.

Antibodies to Neisseria Oligosaccharides, and Diagnosis and Therapy Therewith

Just as the oligosaccharides can be used in vaccines, so to they can be used to generate antibodies to themselves, which antibodies, in turn, can be used to detect that particular strain of bacteria or for passive immunity. Antibodies include but are not limited to polyclonal, monoclonal, chimeric, single chain, Fab fragments, and an Fab expression library. Various procedures known in the art may be used for the production of polyclonal antibodies to oligosaccharide. For the production of antibody, various host animals can be immunized by injection with the oligosaccharide, including but not limited to rabbits, mice, rats, sheep, goats, etc. In one embodiment, the oligosaccharide can be conjugated to an immunogenic carrier, e.g., bovine serum albumin (BSA) or keyhole limpet hemocyanin (KLH). Various adjuvants may be used to increase the immunological response, depending on the host species. For preparation of monoclonal antibodies directed toward the oligosaccharide, or fragment, analog, or derivative thereof, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for an oligosaccharide together with genes from a human antibody molecule of appropriate biological activity can be used; such antibodies are within the scope of this invention. Such human or humanized chimeric antibodies are preferred for use in therapy of human diseases or disorders, since the human or humanized antibodies are much less likely than xenogenic antibodies to induce an immune response, in particular an allergic response, themselves. According to the invention, techniques described for the production of single chain antibodies (U.S. Pat. No. 4,946,778) can be adapted to produce oligosaccharide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an oligosaccharide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific oligosaccharide, one may assay generated hybridomas for a product which binds to an oligosaccharide containing such epitope. For selection of an antibody specific to an oligosaccharide from a particular species or strain of Neisseria, one can select on the basis of positive binding with oligosaccharide expressed by or isolated from cells of that species or strain.

The foregoing antibodies can be used in methods known in the art relating to the localization and activity of the oligosaccharide, e.g., for Western blotting, imaging oligosaccharide in situ, measuring levels thereof in appropriate physiological samples, etc.

Diagnosis of infection with a Gram positive bacterium can use any immunoassay format known in the art, as desired. The antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodide); magnetic resonance shift reagents (such as gadolinium and manganese); or radio-opaque reagents.

Alternatively, the nucleic acids and sequences thereof of the invention can be used in the diagnosis of infection with Neisseria, in particular, to identify a particular, strain, or to determine which, if any, of the glycosyltransferase genes are mutaed. For example, the lgt genes or hybridizable fragment thereof can be used for in situ hybridization with a sample from a subject suspected of harboring an infection of Neisseria bacteria. In another embodiment, specific gene segments of a Neisseria can be identified using PCR amplification with probes based on the lgt genes of the invention. In one aspect of the invention, the hybridization with a probe or with the PCR primers can be performed under stringent conditions, or with a sequence specific for a unique strain or a limited number of strains of the bacterium, or both, thus allowing for diagnosis of infection with that particular strain (or strains). Alternatively, the hybridization can be under less stringent conditions, or the sequence may be homologous in any or all strains of a bacterium, thus allowing for diagnosis of infection with that species.

The present invention will be better understood from a review of the following illustrative description presenting the details of the constructs and procedures that were followed in its development and validation.

EXAMPLE

This Example describes a locus in *Neisseria gonorrhoeae* strain F62 containing five genes. Four of the genes are responsible for the sequential addition of the GalNAcβ1→3Galβ1→4GlcNAcβ1→3Galβ1→4 to the substrate Glcβ1→4Hep→R of the inner core region (Yamasaki et al., 1991, Biochemistry 30:10566). The fifth gene is involved with the addition of the α-linked galactose residue in the biosynthesis of the alternative LOS structure Galα1→4Galβ1→4Glcβ1→4Hep→R (John et al., 1991, J. Biol. Chem. 266:19303). The DNA sequence analysis revealed that the first, third and fourth reading frames contained poly-G tracts which in strain F62 were respectively 17, 10 and 11 bp. Thus, three of the LOS biosynthetic enzymes are potentially susceptible to premature termination by reading-frame changes, as has been reported for the gonococcal pilC genes (Jonsson et al., 1991, EMBO J. 10:477; Rudel et al., 1992, Molec. Microbiol. 6:3439). It is likely that these structural features are responsible for the high-frequency genetic variation of gonococcal LOS (Schneider et al., 1988, Infect. Immun. 56:942).

Materials and Methods

Reagents and chemicals. Most laboratory chemicals were obtained from Sigma Chemical Co (St. Louis, Mo.). Restriction enzymes were purchased from New England Biolabs (Beverly, Mass.).

Media and growth conditions. *E. coli* strains were grown in solid or liquid LB medium (Sambrook et al., 1989, Cold Spring Harbor Laboratory Press, Cold Spring Harbor); antibiotics were added as applicable. Carbenicillin was used at 50 μg/ml and erythromycin at 200 μg/ml. *Neisseria gonorrhoeae* strain F62 was grown on GC agar (Swanson, 1978, Infect. Immun. 19:320) or GC agar containing 2 μg/ml erythromycin. For isolation of LOS or genomic DNA, gonococci were grown in 1.5% proteose peptone broth (Difco Laboratories, Detroit Mich.), 30 mM phosphate, 8.5 mM NaCl supplemented with 1% isovitalex (Becton Dickinson Microbiology Systems, Cockeysville, Md.).

Recombinant DNA methods. Plasmids were purified using either Qiagen columns or the QLAprep spin columns obtained from Qiagen Inc. (Chatsworth, Calif.). Digestion with restriction enzymes, gel electrophoresis, ligations with T4 DNA polymerase and transformation of *E. coli* were done according to Sambrook et al. (Sambrook et al., 1989, Cold Spring Harbor Laboratory Press, Cold Spring Harbor). Southern hybridization was performed on Hybond N+ membranes Amersham Co. (Arlington Heights, Ill.) with DNA labeled using the ECL kit from Amersham Co. Genomic DNA was isolated as described by Moxon et al. (Moxon et al., 1984, J. Clin. Invest. 73:298).

A gene bank of *Neisseria gonorrhoeae* strain F62 genomic DNA was constructed by ligating ca 20 kb fragments obtained by incomplete digestion with Sau3A into BamHI/EcoRI digested λ2001 (Karn et al., 1984, Gene 32:217). The phage library was screened by hybridization with random-primer-labeled plasmid pR10PI, and 5 clones were isolated by plaque purification. The phage from these clones were purified by sedimentation followed by flotation on CsCl (Davis et al., 1980, Cold Spring Harbor Laboratory, Cold Spring Harbor, N.Y.), and the DNA was isolated. From one of these clones, two ClaI fragments of 4.9 and 3.4 kb were isolated by gel electrophoresis and recovery with Geneclean II (BIO 101 Inc., La Jolla, Calif.). These were ligated into ClaI cut pBluescript II SK- from Stratagene (La Jolla, Calif.) and called p4900 and p3400 respectively. p4900 contained a PstI site in the insert and was subdivided into two clones containing inserts of 2.1 and 2.8 kb. The clone containing the 2.8 kb insert was called pPstCla. The inserts in p3400 and pPstCla were sequenced by the chain termination method (Sanger et al., 1977, Proc. Natl. Acad Sci. USA 74:5463) using Sequenase II, (United States Biochemical Co., Cleveland, Ohio). All of the sequence presented in SEQ ID NO:1 was completed in both directions.

Figure 6:
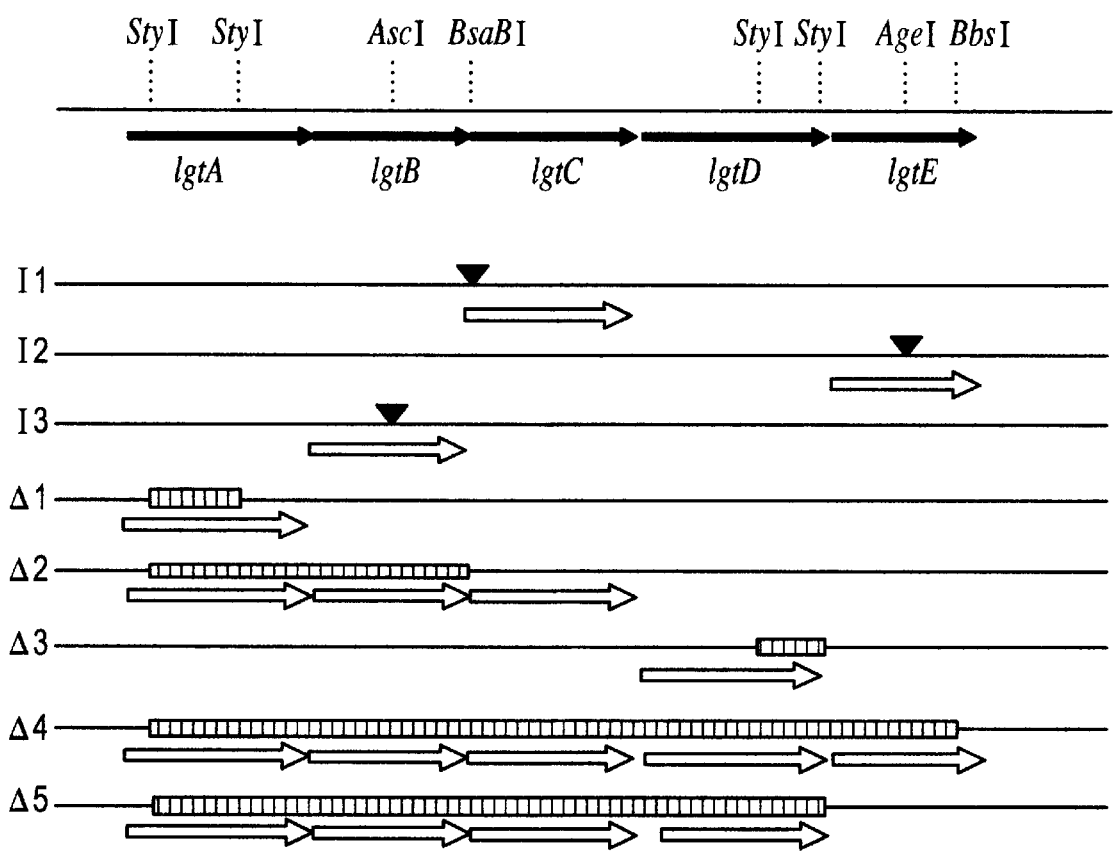
FIG. 6: Deletions in the LOS locus. Three insertion and five deletions of the LOS locus were constructed as detailed in the methods section. The restriction sites that were used are indicated. The insertions are marked by triangles and the extent of the deletions by stippled boxes. The open arrows indicate the open reading frames disrupted by the construction. In each of the constructs the erythromycin marker ermC' was inserted at the site of the insertion or the deletion.

The insertion and deletions shown in FIG. 6 were constructed as follows. I1, I3, Δ1 and Δ2 used plasmid pPstCla cut respectively with BsaBI, AscI, StyI and double cut with StyI and BsaBI. I2 and Δ3 used plasmid p3400 cut with AgeI or StyI. The complete locus was assembled by cloning the ClaI-ApaI fragment from p3400 into pPstCla cut with ClaI and ApaI, and the plasmid was called pLOS5. Deletions Δ4 and Δ5 were constructed using pLOS5 and digestion with StyI and BbsI or with StyI alone. In all instances (except digestion with BsaBI) the cut plasmids were treated with the Klenow fragment of *E. coli* DNA polymerase to blunt the ends, and ermC' (erythromycin resistance marker) was inserted. The ermC' gene was isolated from plasmid pIM13 (Projan et al., 1987, J. Bacteriol. 169:5131) as a ClaI-HindIII fragment and cloned into the same sites in plasmid pHSS6 (Seifert et al., 1986, Proc. Natl. Acad. Sci. USA 83:735). From this plasmid it was excised as a NotI fragment, the ends blunted by treatment with Klenow fragment of DNA polymerase, purified by gel electrophoresis and recovery with Geneclean II.

Transformation of piliated *Neisseria gonorrhoeae* strain F62 was performed with plasmids isolated from *E. coli* (Klugman et al., 1989, Infect. Immun. 57:2066) and the transformants selected on GC agar (Swanson, 1978, Infect. Immun. 19:320) containing 2 μ/ml erythromycin. The fidelity of the genomic alteration of each of the gonococcal transformants was verified by sequencing the upstream and downstream junctions of the ermC' gene in their genomic DNA using a PCR technique. Two 5' biotinylated primers, GCCGAGAAAACTATTGGTGGA (SEQ. ID. NO:9) and AAAACATGCAGGAATTGACGAT) (SEQ. ID. NO:10), were synthesized; these were based on the ermC' sequence near its upstream and its downstream end respectively. The primers were designed such that their 3' ends pointed outward from the ermC' gene. Each of these primers was used together with a suitable primer matching the sequence of the LOS locus near the putative insertion. PCR was performed according the instructions supplied with the GeneAmp PCR Reagent Kit from Perkin Elmer (Branchburg, N.J.) using 25 cycles. In all instances the expected size product was obtained. The DNA sequence of these products was determined by purifying the PCR product on magnetic streptavidin beads from Dynal, Inc. (Lake Success, N.Y.) and sequencing with the Sequenase II kit according to a protocol provided by Dynal, Inc., based on the method developed by Hultman et al (Hultman et al., 1989, Nucleic Acids Res. 17:4937). The sequences were analyzed by computer programs in the GCG package of Genetics Computer Group, Inc. (Madison, Wis.).

Immunological methods. Monoclonal antibodies 17-1-L1 (L1), 9-2-L378 (L3), 2-1-L8 (L8) were obtained as filtered ascites fluids. Antibody 1-1-M was obtained as ascites fluid and 3F11and 4C4 were obtained as tissue culture supernatants. LOS was extracted from each of the gonococcal mutants by the hot phenol-water method (Westphal and Jann, 1965, Academic Press, New York 83–91) and purified as described (Johnston et al., 1976, J. Exp. Med. 143:741). The LOS was diluted to 200 μg/ml in the Western blot buffer described by Towbin et al. (Towbin et al., 1979, Proc. Natl. Acad. Sci. USA 76:4350), and 1.5 μl aliquots were spotted on Immobilon-P membrane from Millipore Corp (Bedford, Mass.) that was lying on 3MM Whatman filter paper (Whatman Ltd., Maidstone, England) soaked in the blotting buffer. The spots were allowed to absorb into the membrane over a period of 2 min and the strips were placed in blocking buffer for at least 60 min. The blocking buffer consisted of 3% gelatin dissolved in 150 mM NaCl, 10 mM Tris-HCl 10 mM pH 7.5, 5 mM $MgCl_2$, 0.02% $NaN_3$. The strips were washed thrice in the same buffer containing 1% gelatin. The strips were treated for 2 h with monoclonal antibodies diluted in blocking buffer. The antibodies available as ascites fluids were diluted 1/1000, antibodies available as tissue culture supernatants 1/10. The strips were washed, incubated for 60 min with a 1/1000 dilution of phosphatase-conjugated anti-IgG,IgA,IgM from Cappel (Organon Teknika Co., West Chester, Pa.), washed and stained as described previously (Blake et al., 1984, Analyt. Biochem. 136:175).

Gel electrophoresis. Gel electrophoresis of LOS samples was performed as described by Lesse et al (Less et al., 1990, J. Immunol. Meth. 126:109) and the gels silver stained (Hitchcock and Brown, 1983, J. Bacteriol. 154–269).

Results

Cloning of the LOS Locus. During attempts to isolate the porin gene of Neisseria gonorrhoeae, pBR322 clones containing a 4.9 kb ClaI fragment that reacted by colony blots with a rabbit antiserum to purified porin were repeatedly isolated. An immunoreactive subclone, pR10PI, consisting of a 1305 bp RsaI-ClaI fragment was derived and its DNA sequence was determined. This sequence had homology to a gene isolated from Haemophilus influenzae called lex-1 (Cope et al., 1991, Molec. Microbiol. 5:1113) or lic2A (High et al., 1993, Molec. Microbiol. 9:1275) that is known to be involved in LPS synthesis of that species. Using subclone pR10PI as a probe, Southern blots of Neisseria gonorrhoeae genomic DNA digested with ClaI revealed hybridization with two fragments, 4.9 and 3.4 kb. However, digestion with some other restriction enzymes gave rise to only a single band. Notably, digestion with BfaI gave rise to a single band of 4.1 kb, suggesting that the two copies were closely linked (data not shown). A λ2001 bank of Neisseria gonorrhoeae strain F62 DNA was screened by hybridization with pR10PI and 5 clones were isolated. One of these clones, when digested with either ClaI or BfaI and examined by Southern hybridization using pR10PI as the probe, gave rise to a pattern identical to that seen with genomic DNA. The appropriate ClaI fragments of this λ2001 clone were isolated and cloned into the ClaI site of pBluescript II SK-. The entire sequence of the 3400 ClaI fragment was determined. Mapping of the clone containing the 4900 bp ClaI fragment indicated that there was a single PstI site in the clone about 2.8 kb from one side, allowing the clone to be divided into two subclones. Partial sequence of the ends of the 2.1 kb subclone indicated that it contained a coding frame homologous to the E. coli COOH-terminal portion of the α subunit of glycyl-tRNA synthetase (glyS) and the majority of the β subunit of this gene (Webster et al., 1983, J. Biol. Chem. 258:10637). The predicted length of DNA needed to match the E. coli sequence was present; this clone was not examined further.

DNA Sequence of the LOS Locus. A summary of the features found by sequencing the two clones is illustrated in FIG. 2. Following the gas gene were found five closely spaced open reading frames. The last frame has 46 bp downstream of the termination codon a sequence typical of a rho independent termination signal. Subsequently, there is an area of ca 100 bp that has striking homology to the IS1106 neisserial insertion sequence (Knight et al., 1992, Molec. Microbiol. 6:1565). Further elucidation of the nature of this locus, presented below, showed the five open reading frames code for LOS glycosyl transferases and hence they have been named lgtA-lgtE.

Searches for internal homology within this locus indicates that the DNA coding for the first two genes (lgtA, lgtB) is repeated as the fourth and fifth genes (lgtD, lgtE) and that interposed is an additional open reading frame, lgtC. This is in keeping with the data obtained by Southern hybridization presented above, in which pR10PI probe containing the lgtB and a small portion of the lgtC gene hybridized with two ClaI fragments, but with only one BfaI fragment (see positions of the BfaI sites in the LOS locus in FIG. 2). In more detail, 16 bp following the stop codon of the tRNA synthetase (glyS) is the beginning of a stem loop structure followed closely by a consensus ribosome binding site (rbs), and within 6 bp is a TTG believed to be the initiation codon of lgtA. 2871 bp downstream from the beginning of the stem loop (closely following the stop codon of lgtC) there is an almost perfect repeat of the stem loop structure, the rbs and the TTG initiation codon of were found with the downstream sequence strongly homologous for about 500 bp. The sequences then diverge to some extent. However, at the beginning of lgtB and lgtE the homology again becomes nearly perfect for ca 200 bases to then diverge toward the latter part of the orfs. The similarity of the homologous proteins is illustrated in FIGS. 3 and 4. These comparisons, demonstrate the near-perfect conservation of the primary structure in the N-terminal portions of the molecules with increasing divergence toward the COOH-termini of the proteins.

The lgtC sequence interposed between the repeated portions of the locus is not repeated within the locus or in the Neisseria gonorrhoeae genome (data not shown). It appears to be homologous to E. coli rfaI or rfaJ genes, which are very closely related genes that serve as glucosyl transferases in core LPS biosynthesis (Pradel et al., 1992, J. Bacteriol. 174:4736). The similarity of rfaI with lgtC is illustrated in FIG. 5.

It was found that three of these genes contained within their coding frame runs of guanosines coding for stretches of glycines (see FIG. 2). These poly-G regions were found in lgtA (17 bp), lgtC (10 bp) and lgtD (11 bp); in each case the number G residues was one that maintained an intact reading frame (see FIGS. 3 and 5). In each of the three genes a change of 1 or 2 G bases would cause premature termination of the trascript.

LOS phenotype of *Neisseria gonorrhoeae* F62 with deletions of the LOS locus. In order to define the function of the lgt genes, insertions or deletions of the LOS locus were constructed in plasmids propagated in *E. coli*. The insertions or deletions in each case were marked with the ermC' gene, which is an excellent selective marker in *Neisseria gonorrhoeae* (Klugman et al., 1989, Infect. Immun. 57:2066). The constructions are summarized in FIG. 6. I1, I2 and I3 refer to insertions of the ermC' marker into, respectively, a BsaBI, AgeI and AscI site. Similarly, the deletions were constructed by excising portions of the plasmids and substituting the erythromycin marker. The open arrows indicate the gene or genes disrupted. Each of these plasmids was used to transform *Neisseria gonorrhoeae* strain F62 and transformants were selected on erythromycin-containing plates. The fidelity of the genomic alteration of a prototype of each of the gonococcal transformants was verified by sequencing the upstream and downstream junction of the ermC' gene. To simplify the nomenclature in this report the gonococcal mutants have been given the same names used to identify the plasmid constructs in FIG. 6.

Figure 7:
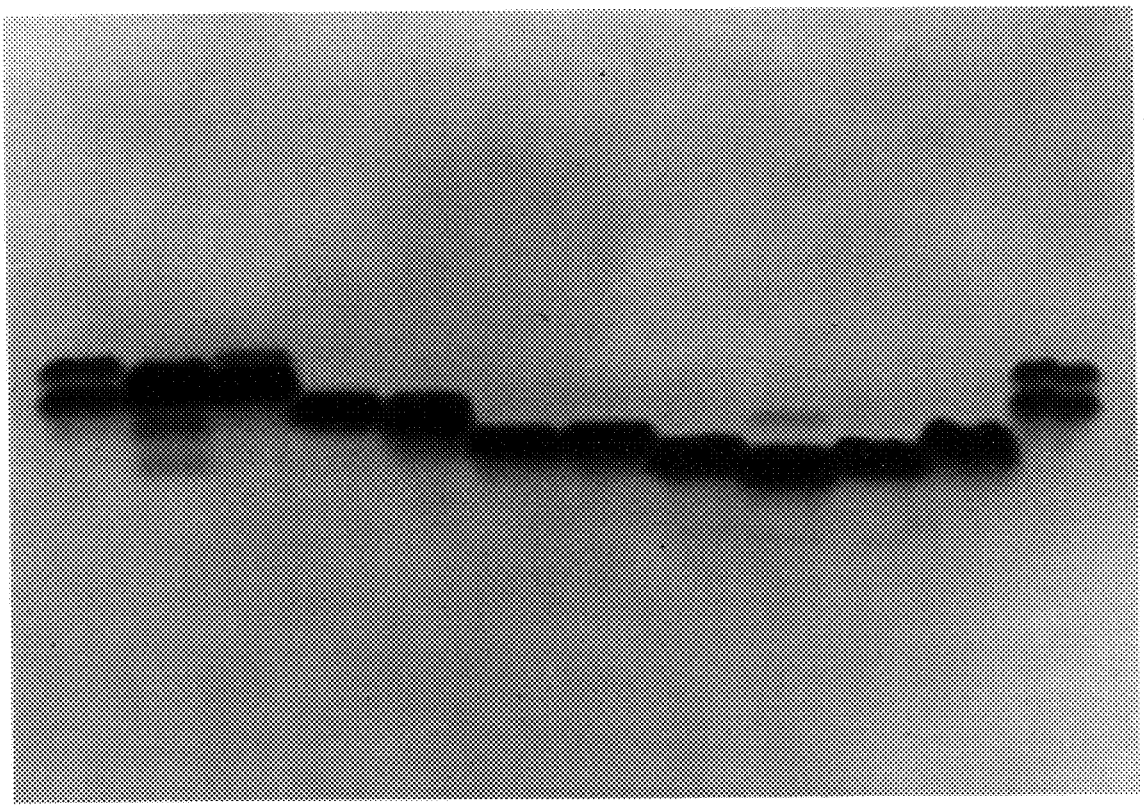
FIG. 7: Silver-stained SDS-PAGE of LOS preparations. Gel electrophoresis of purified LOS samples of 375 ng was performed and stained as described in materials and methods. Above the gel are indicated the structure of the LOS of the major bands inferred to be present in each of the preparations. These structures are based on the reactivity with monoclonal antibodies shown in FIG. 8, but are presented in this Figure to facilitate interpretation of the patterns observed. R stands for the inner core region and lipid A. 1291e is a pyocin resistant mutant (Dudas and Apicella, 1988, Infect. Immun. 56:499)

The LOS of the mutants were examined by SDS-PAGE and compared to the LOS of strain 1291e. This strain was originally isolated by Dudas and Apicella Dudas and Apicella, 1988, Infect. Immun. 56:499) as a pyocin-resistant mutant of strain 1291 wild type and has been extensively characterized both chemically and genetically. Chemical analysis has shown that this mutant lacks completely the lacto-N-neotetraose substitution on heptose 1 (John et al., 1991, J. Biol. Chem. 266:19303). The genetic basis of this mutant has been defined (Zhou et al., 1994, J. Biol. Chem. 269:11162; Sandlin and Stein, 1994, J. Bacteriol. 176:2930); it is a mutation of the pgm gene coding for phosphoglucomutase. This mutation prohibits the synthesis of UDP-glucose and hence the addition of glucose to the heptose. As seen in FIG. 7, the parental wild type F62strain gives rise to two major LOS bands; their appearance is indistinguishable from SDS-PAGE patterns previously published by other workers (Schneider et al., 1985, Amer. Soc. Microbiology, Washington 400–405). The mutants are arranged on the gel according to the size of the major band that they contain. The size decreases from the top band of the F62 wt LOS in four clear steps to the size of the LOS of Δ4 or I2. Since the I2 mutant (with an insertion into lgtE, the last gene in the locus) has the same phenotype as Δ4 (which has a complete deletion of the locus), it suggests that the lgtE product performs the first biosynthetic step. Thus, the enzymes encoded by lgtA-D, although intact, do not have a substrate to act upon. Mutant Δ5 (a deletion of the locus with the exception of lgtE) gives rise to a LOS that is one step larger, supporting the idea that this gene accounts for the initial biosynthetic step. Note that the LOS of both I2 and Δ4 mutants is perceptibly larger than the LOS of strain 1291e which is known to be unable to add glucose, the first residue in the lacto-N-neotetraose chain. These data suggest that lgtE encodes the galactosyl transferase enzyme which adds the first galactose of the lacto-N-neotetraose.

Figure 8:
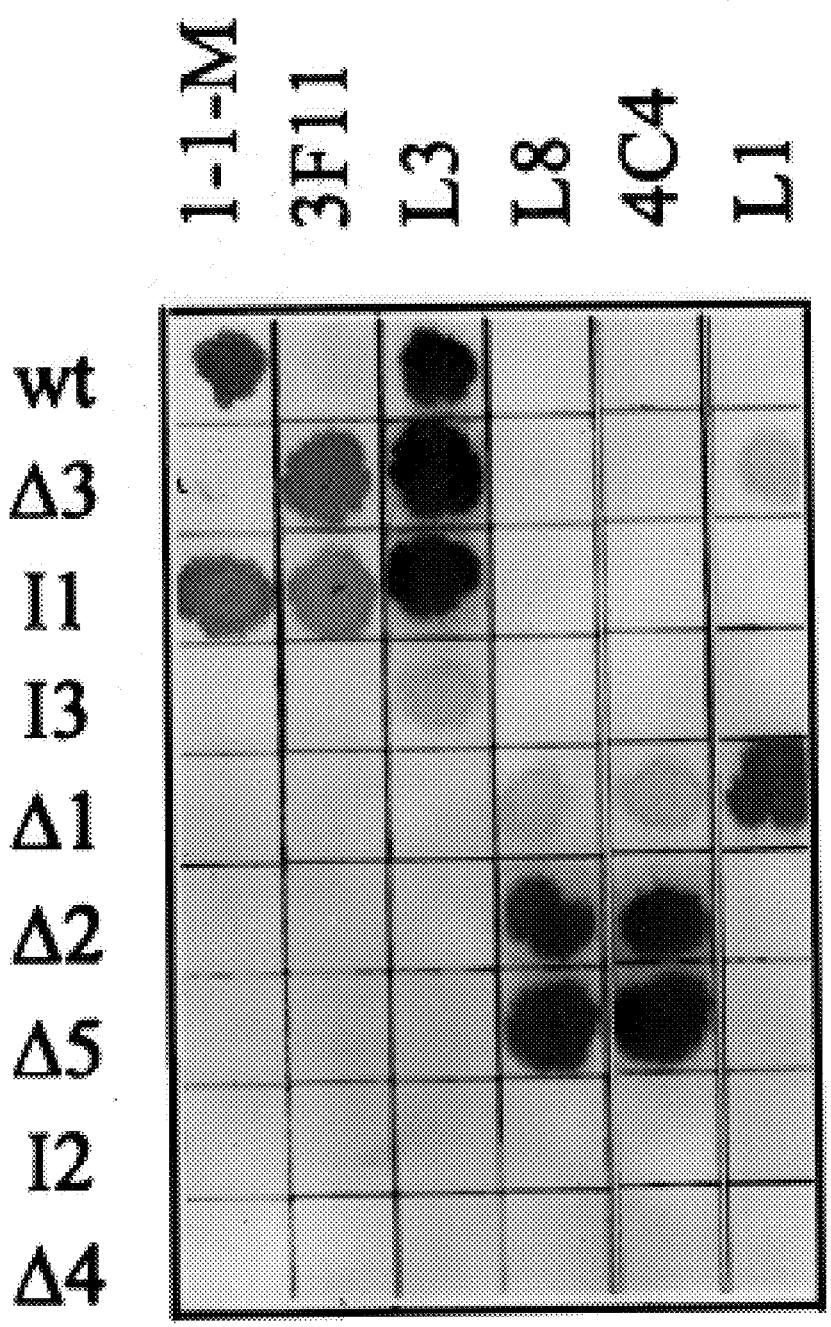
FIG. 8: Reactivity of LOS from strain F62 wt and mutants with monoclonal antibodies. The names of the following monoclonal antibodies were abbreviated: 17-1-L1 (L1), 9-2-L378 (L3), 2-1-L8 (L8). Purified LOS was applied to Immobilon-P membranes, allowed to react with the antibodies and developed as described in materials and methods. The specificity of the monoclonal antibodies is summarized in FIG. 1.

The LOS preparations were also studied using a dot blot technique for their reactivity with monoclonal antibodies. The monoclonal antibodies employed and their reported specificities are shown in FIG. 1. The reactions observed with the LOS obtained from the parental strain and the mutants are summarized in FIG. 8. The reactivity of the parental F62 with 1-1-M, 3F11 and L8 was as reported previously by Mandrell et al (Mandrell et al., 1985, Amer. Soc. Microbiology, Washington 379–384) and by Yamasaki et al (Yamasaki et al., 1991, Mol. Immunol. 28:1233). Mutants Δ4 and I2 fail to react with any of the antibodies. However, Δ5 gives a strong reaction with antibodies 4C4 and L8, indicating that the first galactose residue is present. This is in keeping with the SDS-PAGE results (see FIG. 6) and supports the role of lgtE as the galactosyl transferase. It also indicates that deletions upstream of lgtE do not significantly inactivate its function by polar effects. The LOS of F62 wt parent has strong reactivity with L3 and weak reactivity with 3F11. It is known that reactivity 3F11 is occluded by the addition of the GalNAc residue (Schneider et al., J. Exp. Med. 174:1601); this is not the case with the L3 antibody. The wt LOS reacts with 1-1-M, the antibody reactive when the terminal GalNAc residue is present. The reactivity with 1-1-M is lost in Δ3 which has a deletion only in lgtD. This suggest that this gene encodes the GalNAc transferase.

The reactivity with antibody L1 (specific for the alternative LOS structure capped with an α1→4Gal) is not seen in wt LOS, is absent in I1, and all deletions which affect lgtC. The reactivity is strongest in Δ1, which has a deletion of lgtA only. Note that this mutant also has lost reactivity with 3F11 and L3. These two findings suggest that lgtA codes for the GlcNAc transferase, and when this residue is not added, the incomplete chain is a substrate for the action of lgtC to produce the alternative LOS structure. Note that the sizes of the LOS products seen in FIG. 7 are in accord with the imnmunological data. This conclusion suggests that lgtC encodes the α-Gal transferase. This is further supported by the weak reactivity of mutant Δ3 with antibody L1. Mutant Δ3 has a deletion of lgtD and fails to add the terminal GalNAc, allowing the α-Gal transferase to modify the lacto-N-neotetraose group to produce a $P_i$-like globoside (Mandrell, 1992, Infect. Immun. 60:3017). Mutant I3 (with inactive lgtB) has lost reactivity with 1-1-M, 3F11 and L1, and remains only weakly reactive with L3. Together with the size of the product, these observations suggest that lgtB encodes the galactosyl transferase adding Galβ1→4 to the GlcNAc residue. Ricinus lectin RCA-I is specific for terminal galactose in β linkage (Nicolson and Blaustein, 1972, Biochim. Biophys. Acta 266:543; Lin and Li, 1980, Eur. J. Biochem. 105:453) and was used to confirm the presence of this structure on the LOS preparations. Using ELISA tests it was found that wild type, Δ3, Δ2 and Δ5 LOS, expected to bear a terminal βGal, bound the lectin (see FIG. 7), while Δ4, I2, Δ1 and I3 were unreactive (data not shown).

Discussion

A locus containing 5 open reading frames has been cloned. The effect of eight defined mutations within this locus on the size and serological reactivity of the LOS produced by gonococcal transformants suggests that these genes are the glycosyl transferases responsible for the biosynthesis of most of the lacto-N-neotetraose chain. The data obtained allow an-identification of the function of each of these genes. It is noteworthy that lgtB and lgtE, which are structurally very closely related, also perform an apparently very similar biosynthetic task, i.e. the addition of Galβ1→4 to GlcNAc or Glc, respectively. Similarly, the closely related lgtA and lgtD add GalNAc or GlcNAc β1→3, respectively, to a Gal residue. lgtC, which is unrelated to the other genes in the locus, is responsible for the addition of a Galα1→4.

The DNA sequence showed that three of the genes (lgtA, lgtC and lgtD) contain tracts of guanosines which code for glycine residues in the proteins. These provide a potential mechanism for high-frequency variation of expression of these genes. Slippage in such poly-G tracts is well documented to control the expression of the gonococcal pilC genes, with resultant effects on pilus adhesiveness to human epithelial cells (Rudel et al., 1992, Molec. Microbiol. 6:3439). In strain F62, the numbers of bases in each of the three poly-G regions were such that the proteins are in frame, and this is in keeping with the ability of F62 wild type to produce a complete LOS including the addition of the terminal GalNAc.

Three aspects of LOS biosynthesis appear potentially to be subject to high frequency variation. The first is the addition of the terminal GalNAc (lgtD). This would cause an alteration of reactivity with monoclonal antibody 1-1-M, and this phase variation has been reported by van Putten (Van Putten, 1993, EMBO J. 12:4043). Similarly, a change in lgtA would cause the failure of the addition of GlcNAc to the growing chain and truncate the LOS at the β-lactosyl level. This is a very common form of LOS in gonococci with a 3.6 kilodalton molecule, which confers resistance to the bactericidal effect of normal human serum (Schneider et al., 1985, Infect. Immun. 50:672). It is tempting to speculate that the in vitro variation between variant A and C of MS11$_{mk}$ from the β-lactosyl chain to a complete LOS (which had a selective advantage in vivo in the volunteers) could be explained by regaining functional expression, of the GlcNAc transferase lgtA Finally, the variable addition of α1→4Gal to either the β-lactosyl (p$^k$-like globotriose) or the lacto-N-neotetraose group (P$_i$-like globoside) (Mandrell, 1992, Infect. Immun. 60:3017) would be under the control of the expression of lgtC. The activity of the lgtC transferase appears to compete poorly with the other transferases for precursor and its activity is evident only if either lgtA or lgtD are silent. For the Galα1→4Galβ1→4Glc trisaccharide to be synthesized the GlcNAc transferase lgtA must be inactive and for expression of the P$_i$-like globoside Galα1→4Galβ1→4GlcNAcβ1→3Galβ1→4Glc the GalNAc transferase lgtD must be silent.

Comparable high frequency antigenic variation of *Haemophilus influenzae* LOS has also been noted and has been attributed to changes in translational frame caused by shifts in the number of CAAT repeats in two separate loci, lic1 (Weiser et al., 1989, Cell 59:657) and lic2 (High et al., 1993, Molec. Microbiol. 9:1275). Shifts allowing the expression of the lic2 gene are correlated with the expression of an epitope with the structure Galα1→4Galβ1→. Since the lic2 gene is homologous to lgtB and lgtE the galactosyl transferases which link Galβ1→4 to respectively Glc or GlcNAc, it is likely that this is its function in *Haemophilus influenzae* LOS synthesis. It is remarkable that while both these mucosal pathogens have evolved frame shift mechanisms to cause antigenic variation of the LOS, that the gonococcal homologs of lic2, (lgtB and lgtE) are not the ones that contain poly-G tracts.

While the frame-shift mechanisms discussed above are suited for on/off regulation of gene expression, the structure of the locus also lends itself to more subtle regulation of the level of expression of the genes. It has been demonstrated that growth rate affects the molecular weight distribution and antigenic character LOS species produced (Morse et al., 1983, Infect. Immun. 41:74). While I have not determined the size of the RNA transcripts it is very likely that lgtA, lgtB and lgtC (in the instance where the poly-G tracts are such that the coding frame is maintained) are transcribed together. The termination codon of lgtA and the initiation codon of lgtB in fact overlap, and the distance between the TAA of lgtB and the ATG of lgtC is only 11 bp. Similarly, the stop codon of lgtD and the start codon of lgtE are separated by only 18 bp. Yet the organization is such that if any of the three genes subject to phase variation are in the off configuration, transcription is able to reinitiate effectively at the beginning of the next gene. This ability to reinitiate transcription was clearly seen with the mutations constructed in this study.

The correlation of LOS structure with function is still in its early stages. The major advances in the field have been the development of an understanding of the structure of the molecules and the ability to relate this, often unambiguously, to the reactivity with a number of well-characterized monoclonal antibodies. Added to this is the realization that in the in vivo environment, which provides CMP-NANA, the organism may or may not sialylate the LOS, depending whether the LOS synthesized is a competent acceptor structure. It is well known that sialylation induces a serum-resistant state in many strains. However, the effect of sialylation in local infection is not as well studied. van Putten has shown that sialylation of LOS has a marked inhibitory effect on epithelial cell invasion, without apparently greatly altering adhesion (Van Putten, 1993, EMBO J. 12:4043). His studies suggest that in the mucosal infection, LOS structures that cannot be sialylated may be important for efficient cell invasion. In the context of this report, such structures could be achieved either by the efficient addition of the terminal GalNAc or by shortening the LOS chain by silencing the GlcNAc transferase. The correlation of LOS chemistry with biological reaction has been complicated by the leakiness of the existing LOS mutants isolated by pyocin selection (Dudas and Apicella, 1988, Infect. Immun. 56:499; Sandlin et al., 1993, Infect. Immun. 61:3360). This is in fact exemplified with mutant 1291e which shows in addition to the major low molecular weight band, an additional higher band (see FIG. 7). The new insight provided into the genetics of the biosynthesis of gonococcal LOS will allow construction of mutants that are not leaky. For instance, Δ4 and Δ5 should be stable mutants since they no longer contain genes with poly-G tracts. The expression of the genes containing the poly-G tracts could be stabilized by engineering the areas so that glycines are encoded by other codons.

The present invention is not to be limited in scope by the specific embodiments. described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims. It is also to be understood that all base pair sizes given for nucleotides are approximate and are used for the purpose of description. Various references are cited herein, the disclosures of which are incorporated by reference herein in their entirety.

What is claimed is:

1. A purified nucleic acid that encodes a fragment of a polypeptide having an amino acid sequence of SEQ ID NO:3, SEQ ID NO:4, SEQ ID NO:5, SEQ ID NO:6, SEQ ID NO:8, SEQ ID NO:11 or SEQ ID NO:12, wherein said fragment retains glycosyltransferase activity.

2. The nucleic acid of claim 1, wherein the encoded fragment catalyzes a reaction of:

(a) adding Gal β1→4 to GlcNAc or Glc;

(b) adding GalNAc or GlcNAc β1→3 to Gal; or (c) adding Gal α1→4 to Gal.

3. A nucleic acid vector comprising the nucleic acid of claim 1.

4. An expression vector comprising the nucleic acid of claim 1 operatively associated with an expression control sequence.

5. A recombinant host cell containing the nucleic acid of claim 1 in association with nucleotide sequences non-native to the nucleic acid.

6. A recombinant host cell containing the nucleic acid of claim 1 operatively associated with an expression control sequence non-native to the nucleic acid, wherein the expression control sequence controls expression in the host cell.

7. The recombinant host cell of claim 6 which is prokaryotic.

8. The nucleic acid of claim 1 wherein the polypeptide has the amino acid sequence of SEQ ID NO:3.

9. The nucleic acid of claim 1 wherein the polypeptide has the amino acid sequence of SEQ ID NO:4.

10. The nucleic acid of claim 1 wherein the polypeptide has the amino acid sequence of SEQ ID NO:5.

11. The nucleic acid of claim 1 wherein the polypeptide has the amino acid sequence of SEQ ID NO:6.

12. The nucleic acid of claim 1 wherein the polypeptide has the amino acid sequence of SEQ ID NO:8.

13. The nucleic acid of claim 1 wherein the polypeptide has the amino acid sequence of SEQ ID NO:11.

14. The nucleic acid of claim 1 wherein the polypeptide has the amino acid sequence of SEQ ID NO:12.

15. A method of producing a glycosyltransferase comprising:

(a) culturing the recombinant host cell of claim 6 under conditions that allow expression of the glycosyltransferase; and (b) recovering the expressed glycosyltransferase.

16. The method of claim 15, wherein the glycosyltransferase produced is LOS glycosyltransferase A (lgtA).

17. The method of claim 15, wherein the glycosyltransferase produced is LOS glycosyltransferase B (lgtB).

18. The method of claim 15, wherein the glycosyltransferase produced is LOS glycosyltransferase C (lgtC).

19. The method of claim 15, wherein the glycosyltransferase produced is LOS glycosyltransferase D (lgtD).

20. The method of claim 15, wherein the glycosyltransferase produced is LOS glycosyltransferase E (lgtE).

* * * * *